United States Patent
Miki

(10) Patent No.: US 12,256,892 B2
(45) Date of Patent: Mar. 25, 2025

(54) OPTICAL SYSTEM, METHOD FOR MANUFACTURING OPTICAL SYSTEM, AND ENDOSCOPE

(71) Applicant: OLYMPUS CORPORATION, Tokyo (JP)

(72) Inventor: Takehiro Miki, Fuchu (JP)

(73) Assignee: OLYMPUS CORPORATION, Tokyo (JP)

(*) Notice: Subject to any disclaimer, the term of this patent is extended or adjusted under 35 U.S.C. 154(b) by 512 days.

(21) Appl. No.: 17/731,516

(22) Filed: Apr. 28, 2022

(65) Prior Publication Data

US 2022/0248940 A1  Aug. 11, 2022

Related U.S. Application Data

(63) Continuation of application No. PCT/JP2019/043370, filed on Nov. 6, 2019.

(51) Int. Cl.
| | |
|---|---|
| *A61B 1/00* | (2006.01) |
| *G02B 3/00* | (2006.01) |
| *G02B 13/00* | (2006.01) |
| *G02B 23/24* | (2006.01) |
| *G02B 23/26* | (2006.01) |

(52) U.S. Cl.
CPC ........ *A61B 1/00096* (2013.01); *G02B 3/0087* (2013.01); *G02B 13/0095* (2013.01); *G02B 23/2446* (2013.01); *G02B 23/26* (2013.01)

(58) Field of Classification Search
CPC .... G02B 23/26; G02B 23/2446; G02B 13/18; G02B 13/0095; G02B 3/007; A61B 1/005; A61B 1/002; A61B 1/055; A61B 1/00096; A61B 1/0019
See application file for complete search history.

(56) References Cited

U.S. PATENT DOCUMENTS 6,631,220 B1   10/2003   Liang et al.

FOREIGN PATENT DOCUMENTS

| EP | 3 098 635 A1 | 11/2016 |
|---|---|---|
| JP | H07-146435 A | 6/1995 |
| JP | 2001-507251 A | 6/2001 |
| JP | 2015-138245 A | 7/2015 |

(Continued)

OTHER PUBLICATIONS

International Search Report dated Jan. 7, 2020 received in PCT/JP2019/043370.

*Primary Examiner* — Christopher Stanford
*Assistant Examiner* — Journey F Sumlar
(74) *Attorney, Agent, or Firm* — Scully, Scott, Murphy & Presser, P.C.

(57) ABSTRACT

An optical system includes a plurality of lenses. The plurality of lenses have refractive index distributions in which a refractive index changes in directions orthogonal to optical axes. The optical axes of the plurality of lenses are disposed on the same straight line as each other. The plurality of lenses are manufactured on the basis of same design values relating to an on-axis refractive index and a refractive index distribution constant. When rotation positions around the optical axes of the plurality of lenses at which a total aberration amount of the plurality of lenses reaches a maximum are set as reference rotation positions for the plurality of lenses, any one of the plurality of lenses is arranged at a position acquired by relatively rotating the reference rotation position around the optical axis.

17 Claims, 15 Drawing Sheets

(56) References Cited

FOREIGN PATENT DOCUMENTS

| | | | |
|---|---|---|---|
| JP | 2018-516391 | A | 6/2018 |
| WO | 1998/023984 | A2 | 6/1998 |
| WO | 2016/193051 | A1 | 12/2016 |
| WO | 2019/134953 | A1 | 7/2019 |

# OPTICAL SYSTEM, METHOD FOR MANUFACTURING OPTICAL SYSTEM, AND ENDOSCOPE

CROSS REFERENCE TO RELATED APPLICATIONS

This application is a continuation application based on a PCT Patent Application No. PCT/JP2019/043370, filed Nov. 6, 2019, the entire content of which are hereby incorporated by reference.

BACKGROUND OF THE INVENTION

Field of the Invention

The present invention relates to an optical system, a method for manufacturing an optical system, and an endoscope.

Description of the Related Art

For example, in an endoscope, a flexible scope with an insertion part that is bendable and a rigid scope with an insertion part that is not easily bent are known.

The insertion part of the flexible scope is long enough to be inserted deeply into a test object. In the flexible scope, a distal end part having an optical system for observation at a distal end of a bending part that can be operated from the outside is provided. Since the flexible scope has the bending part that can be operated from the outside, an outer diameter of the insertion part cannot be configured to be very small.

On the other hand, the rigid scope does not have a bending part, and thus, by using an optical system having a small diameter, an outer diameter of the insertion part can be configured to be smaller than that of the flexible scope.

For example, as optical systems, a relay lens optical system, a fiber bundle acquired by binding many optical fibers, a gradient index lens (GRIN lens) having a refractive index distribution in which a refractive index changes in a direction orthogonal to an optical axis, and the like are known.

Although the relay lens optical system has superior image quality, it is difficult to reduce the diameter thereof, and thus the relay lens optical system is not appropriate for a rigid scope having a small diameter.

The gradient index lens is superior to a fiber bundle in terms of image quality and a manufacturing cost as long as the length of an optical path is not too long, and thus is appropriate for a rigid scope having a small diameter.

For example, in Japanese Unexamined Patent Application, First Publication No. H7-146435, it is described that an optical relay including a plurality of radial-direction gradient index lenses has a radial-direction gradient index lens with a negative Abbe number. Here, "radial-direction gradient index lens" refers to a gradient index lens having a refractive index distribution in which a refractive index changes in a direction orthogonal to an optical axis.

In this optical relay, a chromatic aberration in an axial direction is corrected by the lens with the negative Abbe number, and thus the image quality of a color image is improved.

SUMMARY

An optical system a flexible scope according to a first aspect of the present invention includes a plurality of lenses having refractive index distributions in which each of a refractive indexes changes in directions orthogonal to each of optical axes. The optical axes of the plurality of lenses are disposed on the same straight line as each other. The plurality of lenses are manufactured on the basis of the same design values relating to an on-axis refractive index and a refractive index distribution constant. When rotation positions around the optical axes of the plurality of lenses at which a total aberration amount of the plurality of lenses reaches a maximum are set as reference rotation positions for the plurality of lenses, any one of the plurality of lenses is arranged at a position acquired by relatively rotating the reference rotation position around the optical axis.

A method for manufacturing an optical system according to a second aspect of the present invention includes forming a plurality of lenses by cutting a lens base material having a specific refractive index distribution in which a refractive index changes in a direction orthogonal to an optical axis in a direction intersecting the optical axis, and arranging the plurality of lenses such that, when rotation positions around optical axes of the plurality of lenses at which a total aberration amount of the plurality of lenses reaches a maximum are set as reference rotation positions for the plurality of lenses, a state in which any one of the plurality of lenses is relatively rotated around the optical axis with respect to the reference rotation position is formed, and the optical axes of the plurality of lenses are positioned on the same straight line as each other.

An endoscope according to a third aspect of the present invention includes the optical system according to the first aspect.

DETAILED DESCRIPTION OF THE PREFERRED EMBODIMENTS

Hereinafter, embodiments of the present invention will be described with reference to the attached drawings. In all the drawings, as well as in different embodiments, the same reference signs will be assigned to members that are the same as or correspond to each other, and common description will be omitted.

First Embodiment

An endoscope according to a first embodiment of the present invention will be described.

Figure 1:
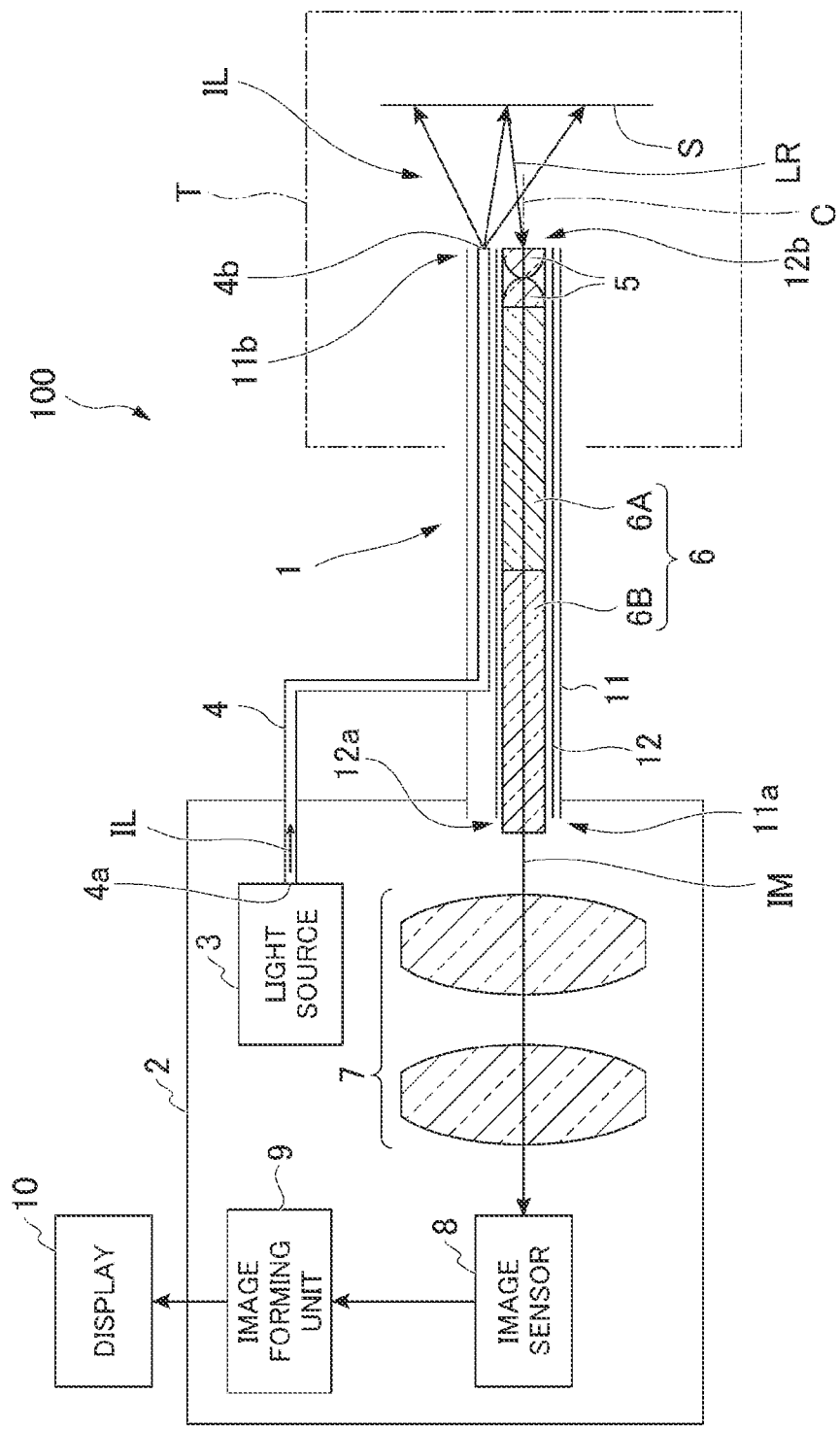
FIG. 1 is a schematic cross-sectional view showing an example of an optical system and an endoscope according to a first embodiment of the present invention.

FIG. 1 is a schematic cross-sectional view showing an example of an optical system and an endoscope according to the first embodiment of the present invention.

The endoscope 100 according to this embodiment shown in FIG. 1 is a rigid scope used for the purpose of observation of the inside of a test object T. The test object T of the endoscope 100 is not particularly limited. For example, the test object T observed using the endoscope 100 may be a human body, a bio tissue, or the like or may be an industrial product, a bridge, an airplane, or the like.

The endoscope 100 includes a casing 2, a display 10, and an insertion part 1.

The casing 2 is disposed outside the test object T. Inside the casing 2, a light source 3, an imaging optical system 7 (an optical system), an image sensor 8, and an image forming unit 9 are housed.

The light source 3 generates illumination light IL for illuminating an observation target using the endoscope 100. A wavelength of the illumination light IL is not particularly limited. A wavelength band of the illumination light IL may be set in accordance with a type and the like of an observation target. For example, the illumination light IL may be monochromatic light or white light. The illumination light IL may be narrow-band light having an appropriate center wavelength.

The wavelength or the center wavelength of the illumination light IL may be either in a visible range or in a non-visible range such as a wavelength range of infrared light or the like.

The device configuration of the light source 3 is not particularly limited as long as it can generate the illumination light IL. For example, as the light source 3, an LED, a laser element, a halogen light source, a xenon light source, or the like may be used.

A light guide 4 transmitting the illumination light IL is connected to the light source 3. The light source 3 includes a light condensing optical system (not shown) that condenses the illumination light IL and optically coupling the illumination light IL on a first end face 4a of the light guide 4.

The light guide 4, for example, has an optical fiber or an optical fiber bundle. The illumination light IL that is optically coupled on the first end face 4a is transmitted through the inside of the light guide 4 and exits from a second end face 4b on a side opposite to the first end face 4a in a longitudinal direction of the light guide 4 to a side in front of the second end face 4b. For example, in a case in which the imaging optical system and the gradient index lens group have an additional function for propagation of illumination light like a laser confocal endoscope, an OCT endoscope, or the like, the light guide 4 is not necessarily essential.

The imaging optical system 7 condenses image light IM transmitted by an optical system inside the insertion part 1 to be described below. The configuration of the imaging optical system 7 is not particularly limited as long as it can focus the image light IM onto an imaging surface of the image sensor 8 to be described below. For example, as the imaging optical system 7, one or more lenses having appropriate refractive power as a whole are used.

The image sensor 8 performs photoelectric conversion of the image light IM condensed using the imaging optical system 7, thereby generating an image signal. As the image sensor 8, for example, a CMOS image sensor, a CCD image sensor, or the like may be used.

The image signal generated by the image sensor 8 is transmitted to the image forming unit 9 to be described below.

The image forming unit 9 converts an image signal transmitted from the image sensor 8 into output image data. When an image signal is converted into output image data, the image forming unit 9 may perform image processing as necessary. The image data is transmitted to the display 10 to be described below.

The display 10 is connected to the image forming unit 9 to be able to communicate therewith. The display 10 has a display screen and displays image data transmitted from the image forming unit 9 on the display screen. The device configuration of the display 10 is not particularly limited. For example, as the display 10, a liquid crystal display, an organic EL display, or the like may be used.

The insertion part 1 is inserted into the inside of a test object T. An outer shape of the insertion part 1 is a bar shape extending outward from the casing 2.

In the example shown in FIG. 1, the insertion part 1 includes an outer cylinder 11 and an inner cylinder 12.

For example, the outer cylinder 11 is formed using a rigid material such as a metal or the like. A first end part 11a of the outer cylinder 11 is open to the inside of the casing 2. A second end part 11b on aside opposite to the first end part 11a in the longitudinal direction of the outer cylinder 11 is open to an outer part.

Inside the outer cylinder 11, the inner cylinder 12 having an outer diameter smaller than an inner diameter of the outer cylinder 11 is disposed.

A first end part 12a of the inner cylinder 12 is positioned inside the casing 2. A second end part 12b on a side opposite to the first end part 12a in the longitudinal direction of the inner cylinder 12 faces an opening of the second end part 11b of the outer cylinder 11.

In the example illustrated in FIG. 1, the second end parts 11b and 12b are drawn to form an opening that is orthogonal to the longitudinal direction. The second end parts 11b and 12b may form a needle-shaped opening that is obliquely inclined with respect to the longitudinal direction.

The inner cylinder 12 holds a gradient index lens group 6 (a plurality of lenses, an optical system) and an objective optical system 5 (an optical system) to be described below inside. An optical axis of each of the gradient index lens group 6 and the objective optical system 5 is disposed on a center axis line C passing through the center of the inner cylinder 12.

The shape of the inner cylinder 12 is not particularly limited as long as it is a cylinder shape that can hold the gradient index lens group 6 and the objective optical system 5 inside.

An inner peripheral part of the inner cylinder 12 has a shape that can house the gradient index lens group 6 to be able to rotate around a center axis line C. A shape of an outer peripheral part of the inner cylinder 12 is not particularly limited as long as it is a shape that is able to be disposed inside the outer cylinder 11.

For example, the inner cylinder 12 may be a member having a circular cylinder shape or may be a member acquired by processing a part of a circular cylinder. For example, the inner cylinder 12 may be formed in a shape in which an opening is formed on a side face of a circular cylinder. For example, the inner cylinder 12 may be formed in a shape acquired by processing an inner peripheral face and an outer peripheral face of a circular cylinder in a concave-convex shape.

For example, the inner cylinder 12 may be configured by a tubular member with a polygonal shape in cross section.

A material of the inner cylinder 12 is not particularly limited. For example, as the material of the inner cylinder 12, a plastic, a metal, or the like may be used. It is preferable that the material of the inner cylinder 12 be a material to which a glass material can be bonded using a resin adhesive.

In the following description, as an example, the inner cylinder 12 will be assumed to be a circular cylinder. In this case, a center axis line C coincides with a center axis line of an inner peripheral face of the circular cylinder.

Inside the outer cylinder 11, near the inner cylinder 12, the light guide 4 described above is disposed in parallel with the inner cylinder 12. In the example illustrated in FIG. 1, the light guide 4 extending to the outside of the casing 2 is inserted into the inside of the outer cylinder 11 from a side part of the outer cylinder 11 near the first end part 11a. The light guide 4 inside the outer cylinder 11 extends to the second end part 11b in parallel with the inner cylinder 12. The second end face 4b of the light guide 4 faces an opening in the second end part 11b of the outer cylinder 11. Near the second end part 11b, the optical axis of the light guide 4 and the center axis line of the inner cylinder 12 are parallel to each other.

The objective optical system 5 is stored near the second end part 12b inside the inner cylinder 12.

The objective optical system 5 condenses reflected light LR of illumination light IL illuminated to a surface S of an observation target in a test object T. The configuration of the objective optical system 5 is not particularly limited as long as the reflected light LR can be condensed and optically coupled to the gradient index lens group 6. For example, as the objective optical system 5, one or more lenses having appropriate refractive power as a whole are used.

In a case in which optical performances that are necessary for the endoscope 100, for example, a magnification, a size of a visual field, resolution, an operating distance, and the like, is acquired by the imaging optical system 7 and the gradient index lens group 6 to be described below, the objective optical system 5 may be omitted.

The gradient index lens group 6 includes a plurality of lenses having refractive index distributions in which a refractive index changes in a direction orthogonal to the optical axis. As the gradient index lens, a lens of which a refractive index changes along an optical axis (in an optical axis direction) (an axial-direction gradient index distribution lens) is also known. However, lenses used for the gradient index lens group 6 are lenses (radial-direction gradient index lenses) having a refractive index distribution in which a refractive index changes in the direction orthogonal to the optical axis as described above. In this specification, unless mentioned otherwise, "gradient index lens" refers to a radial-direction gradient index lens.

A plurality of lenses used in the gradient index lens group 6 are gradient index lenses manufactured for the purpose of causing a refractive index in a refractive index distribution thereof to change in a direction orthogonal to the optical axis and not to change in the direction of the optical axis. Such gradient index lenses have a refractive index distribution having axial symmetry around the optical axis on a cross-section orthogonal to the optical axis in a case in which imbalance due to manufacturing error is excluded. This refractive index distribution does not change in the direction of the optical axis in a case in which imbalance due to manufacturing error is excluded.

On the other hand, in lenses manufactured using an optical material that has a constant refractive index in a case in which manufacturing error is excluded (referred to as constant refractive index lenses), in accordance with an inter-face distance of lens faces being changed in accordance with a distance from the optical axis in the radial direction, an optical path length changes in a radial direction. In accordance with this, the refractive power of the lenses is formed using an optical material of which a refractive index is constant. In this case, an aberration of non-axial symmetry of a single lens due to manufacturing error occurs mainly due to shape error of a lens face, eccentricity of a lens face, and the like occurring in the non-axial symmetry. For this reason, an aberration of non-axial symmetry of each constant refractive index lens is unique to the lens.

The number of lenses of the gradient index lens group 6 is not particularly limited, and lenses of an appropriate number of two or more are used.

In the example illustrated in FIG. 1, the number of gradient index lenses of the gradient index lens group 6 is two. More specifically, in the gradient index lens group 6, a first lens 6A (lens) and a second lens 6B (lens) are disposed in that order from an object side (a second end part 12b side) to an image side (a first end part 12a side). An end part of the image side of the second lens 6B extends to an image side from the first end part 12a.

FIG. 1 shows an example in which there is no gap between the first lens 6A and the second lens 6B, and in which there is no gap between the second lens 6B and the objective optical system 5 in the direction of the optical axis. However, an appropriate air gap or an adhesive layer may be provided between the first lens 6A and the second lens 6B, and between the second lens 6B and the objective optical system 5.

In this embodiment, the objective optical system 5, the gradient index lens group 6, and the imaging optical system 7 configure an optical system.

Next, a detailed configuration of the first lens 6A and the second lens 6B will be described.

Figure 2:
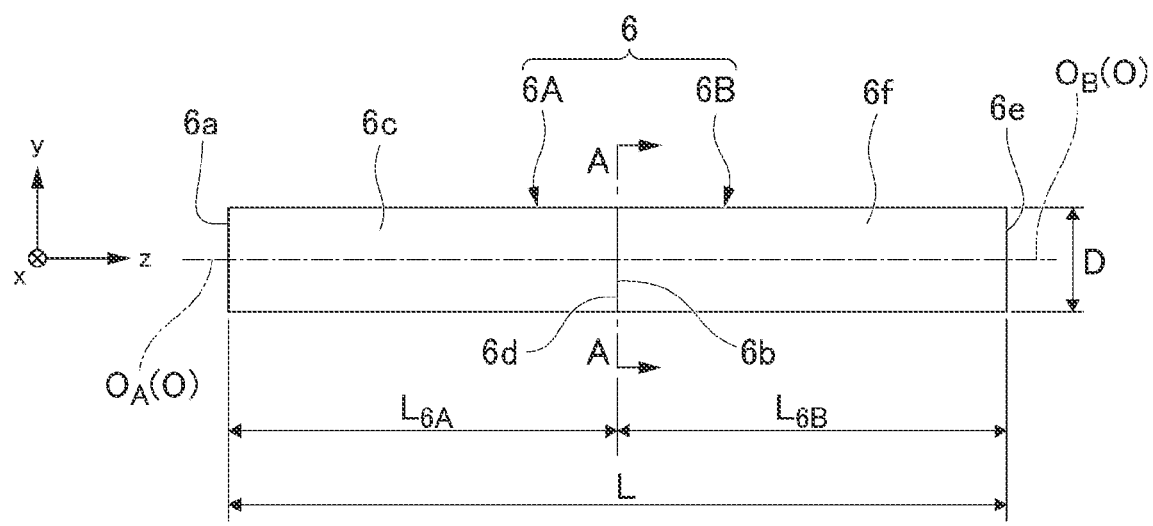
FIG. 2 is a schematic front view showing a gradient index lens group in an optical system according to the first embodiment of the present invention.
Figure 3:
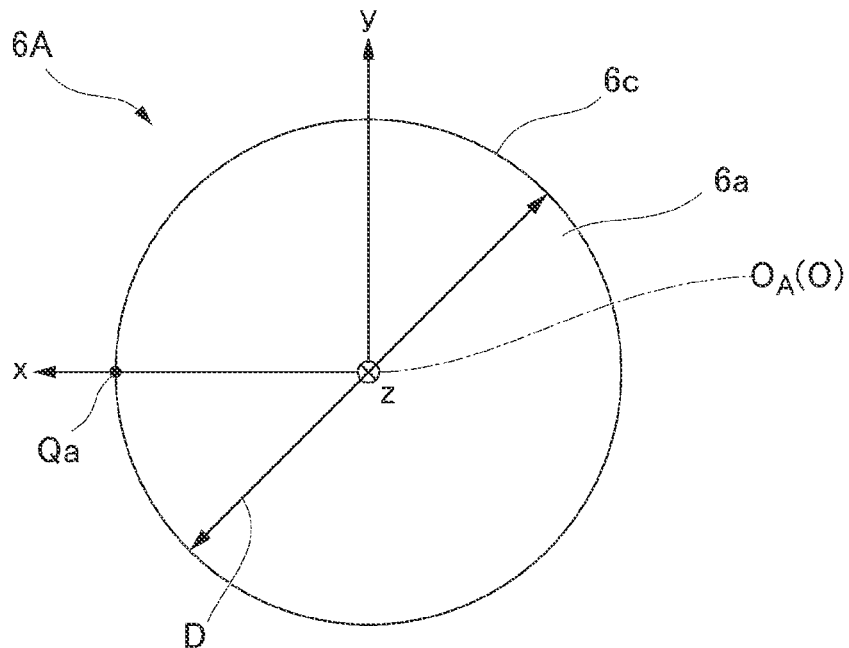
FIG. 3 is a schematic left side view of a gradient index lens according to the first embodiment of the present invention.
Figure 4:
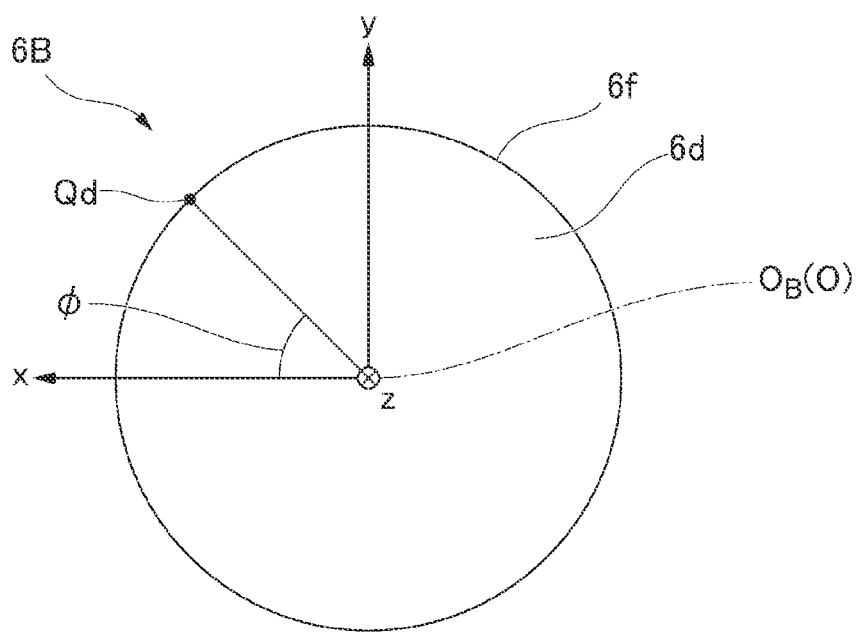
FIG. 4 is a cross-sectional view of FIG. 2 along line A-A.

FIG. 2 is a schematic front view showing the gradient index lens group in the optical system according to the first embodiment of the present invention. Here, FIG. 2 is drawn with the object side as a left side and the image side as a right side and thus has directions different from those of FIG. 1. FIG. 3 is a schematic left side view of the gradient index lens according to the first embodiment of the present invention. FIG. 4 is a cross-sectional view of FIG. 2 along A-A.

As shown in FIG. 2, an outer shape of the first lens 6A is a circular column having an optical axis $O_A$ as its axis and includes a first end face 6a, a second end face 6b, and an outer peripheral face 6c. The first end face 6a and the second end face 6b are end faces of the first lens 6A on the object side and the image side. Both the first end face 6a and the second end face 6b are planes orthogonal to the optical axis $O_A$. The first end face 6a and the second end face 6b, for example, are smoothed using polishing or the like.

A length of the first lens 6A (a distance between the first end face 6a and the second end face 6b) is $L_{6A}$.

As illustrated in FIG. 3, the outer peripheral face 6c is a circular cylinder face having the optical axis $O_A$ as its axis. An outer diameter D of the outer peripheral face 6c is slightly smaller than an inner diameter of the inner peripheral face of the inner cylinder 12 such that the first lens 6A is able to be slidably fitted into the inner cylinder 12.

As illustrated in FIG. 2, an outer shape of the second lens 6B is a circular column having an optical axis $O_B$ as its axis and includes a first end face 6d, a second end face 6e, and an outer peripheral face 6f. The first end face 6d and the second end face 6e are end faces of the second lens 6B on an object side and an image side. Both the first end face 6d and the second end face 6e are planes orthogonal to the optical axis $O_B$. The first end face 6d and the second end face 6e, for example, are smoothed using polishing or the like.

A length of the second lens 6B (a distance between the first end face 6d and the second end face 6e) is $L_{6B}$.

As shown in FIG. 3, the outer peripheral face 6f is a circular cylinder face having the optical axis $O_B$ as its axis. An outer diameter of the outer peripheral face 6f is D that is the same as the outer diameter of the first lens 6A.

As shown in FIG. 2, the first lens 6A and the second lens 6B are disposed with adjacent to each other and disposed on the same axis as each other, in a state that the second end face 6b and the first end face 6d in contact with each other. In other words, the optical axes $O_A$ and $O_B$ are disposed on the same straight line as each other.

In this embodiment, the gradient index lens group 6 is on the same axis as the objective optical system 5 and the imaging optical system 7. For this reason, the objective optical system 5, gradient index lens group 6, and imaging optical system 7 configure a coaxial optical system, and the optical axis of each is the same as the optical axis O of the entire optical system.

Hereinafter, when a positional relation in the gradient index lens group 6 is described, there are cases in which an xyz right-handed orthogonal coordinate system (hereinafter referred to as an xyz coordinate system) fixed to the gradient index lens group 6 is referred to.

A z axis is a coordinate axis extending from the object side to an image side along the optical axis O. An x axis and a y axis are coordinate axes that are orthogonal to each other and are orthogonal to a z axis. An origin of the xyz coordinate system, for example, is disposed at an intersection between the first end face 6a and the optical axis O.

The gradient index lens group 6 which is configured of the first lens 6A and the second lens 6B is a gradient index lens having a circular column shape of which a length is L ($L=L_{6A}+L_{6B}$) as a whole.

As the first lens 6A and the second lens 6B, gradient index lenses manufactured for the purpose of having the same refractive index distribution as each other are used. In other words, in a case in which there is no manufacturing error, the refractive index distributions of the first lens 6A and the second lens 6B are the same as each other. For this reason, as shown in FIG. 1, in a case in which the second end face 6b and the first end face 6d are brought into contact with each other without a gap, the gradient index lens group 6 has the same optical performance as one gradient index lens having a length L.

However, as will be described below, in this embodiment, by adjusting rotation positions of the first lens 6A and the second lens 6B rotating around the optical axis O, aberrations are reduced.

Also in a case in which the gradient index lens group 6 includes three or more gradient index lenses, gradient index lenses manufactured for the purpose of having the same refractive index distribution as each other are used.

It is more preferable that a sum L of lengths of a plurality of lenses of the gradient index lens group 6 and an outer diameter D of a plurality of lenses of the gradient index lens group 6 satisfy Equation (13).

$$\frac{L}{D} > 60 \tag{13}$$

In a case in which the gradient index lens group 6 is used for an endoscope for a medical or industrial use, it is important that it be easy to insert the gradient index lens group 6 into a test object T. and it be easy to position a distal end thereof at a deep inner part of the test object T after insertion. In a case in which L/D is less than 60, a range in which the distal end is brought into contact becomes too short compared to the size of an opening of D or more required for insertion.

A more preferable value of D is 1 mm or less. At this time, L becomes 60 mm or more, and it becomes easy for the gradient index lens group 6 to be close to an observation target inside the test object T through a narrow opening.

In the gradient index lens group 6, although the outer diameter D may not be constant, it is more preferable that the outer diameter D be constant for easy assembly.

Here, a refractive index distribution of the gradient index lens used as the first lens 6A and the second lens 6B will be described.

Figure 5:
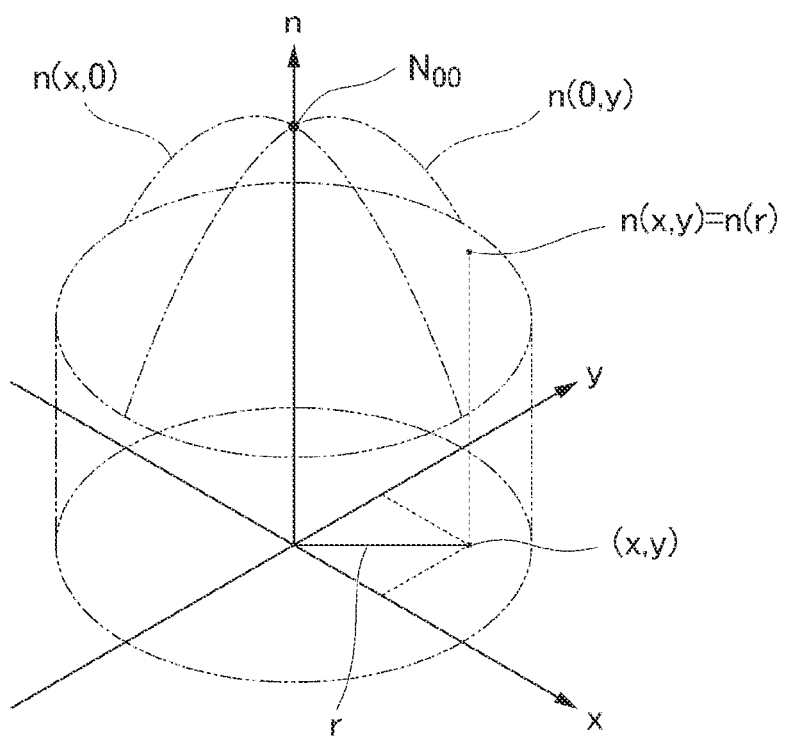
FIG. 5 is a schematic graph showing an example of an ideal refractive index distribution that is a target for a gradient index lens.
Figure 6:
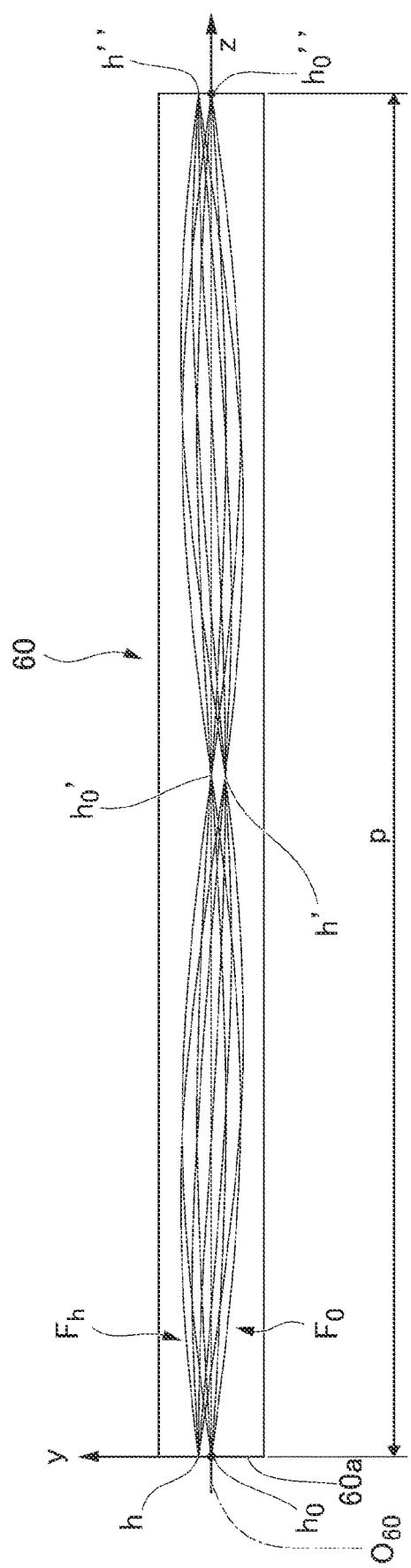
FIG. 6 is a schematic ray tracing diagram in a gradient index lens.

FIG. 5 is a schematic graph showing an example of an ideal refractive index distribution of a gradient index lens. In FIG. 5, an x axis and a y axis as horizontal axes represent an x axis and a y axis of the xyz coordinate system. A horizontal axis represents a refractive index of the gradient index lens. FIG. 6 is a schematic ray tracing diagram in a gradient index lens.

A refractive index distribution n(x, y) on a cross-section orthogonal to an optical axis of a gradient index lens is, as represented in the following Equation (a), represented as a paraboloid of revolution having an optical axis as a center axis. When $r=\sqrt{(x^2+y^2)}$, $n(x, y)$ is represented as in the following Equation (b) depending only on a variable r in polar coordinates (r, θ).

$$n(x, y) = N_{00}\left\{1 - \frac{\sqrt{A}^2}{2}(x^2 + y^2)\right\} \quad (a)$$

$$n(r) = N_{00}\left\{1 - \frac{\sqrt{A}^2}{2}r^2\right\} \quad (b)$$

Here, $N_{00}$ is an on-axis refractive index, and $\sqrt{A}$ is a refractive index distribution coefficient.

In this way, in a case in which there is no manufacturing error, the refractive index distribution of a gradient index lens is defined using the on-axis refractive index is $N_{00}$, and the refractive index distribution coefficient $\sqrt{A}$.

For this reason, between gradient index lenses having manufacturing error, an on-axis refractive index $N_{00}$ and a refractive index distribution coefficient $\sqrt{A}$ are measured, and, in a case in which a difference between values thereof is only about the manufacturing error, it can be regarded that the gradient index lenses have a refractive index distribution manufactured based on the same design value.

For example, the refractive index distribution coefficient $\sqrt{A}$ can be measured using a method as described in Japanese Unexamined Patent Publication No. 2005-289775. First, a gradient index lens is cut out into an appropriate length as necessary, and both end faces are mirror-polished in parallel to each other. Thereafter, an optical chart and the like are brought into contact with one end face of the gradient index lens. An image of the optical chart is observed from an end face of the gradient index lens on the opposite side, and a length (for example, one pitch) m corresponding to one period from that position is acquired. The refractive index distribution coefficient $\sqrt{A}$ is calculated from a relation of $\sqrt{A}=2\pi/m$.

In a case in which the gradient index lens after mirror polishing is shorter than a length corresponding to 0.5 period, and thus the image of the chart brought into contact with one end face cannot be formed, $\sqrt{A}$ may be acquired as the following method. Parallel light is caused to be incident to the gradient index lens, and a position at which the light forms a spot is measured. A length corresponding to 0.25 period may be acquired from the position of the spot, and the acquired length may be converted into a length m corresponding to one period.

Even in the case of the refractive index distribution coefficient $\sqrt{A}$ of a gradient index lens manufactured on the basis of the same design value, it is known that, actually, the refractive index distribution coefficient $\sqrt{A}$ includes manufacturing error. The manufacturing error included in the refractive index distribution coefficient $\sqrt{A}$ is absorbed by adjusting the length of the gradient index lens, and thus a degree of the manufacturing error of the refractive index distribution coefficient $\sqrt{A}$ can be known from a length tolerance of the manufacturer.

For example, in a catalog of GRINTECH Corp, it is written that there is a tolerance, that is, a manufacturing error of ±5% (a width 10%), in the length of the gradient index lens. Having error of a width of 10% in the length of the gradient index lens represents m having error of a width of 10%.

In this case, when a minimum value of m in manufacturing error is denoted by $m_{min}$, and a maximum value of m is denoted by $m_{max}$, $m_{max}=1.1\times m_{min}$. In accordance with this, a minimum value $\sqrt{A}-$ of $\sqrt{A}$ in the manufacturing error is $\sqrt{A}-=2\pi(1.1\times m_{min})$, and a maximum value $\sqrt{A}+$ is $\sqrt{A}+=2\pi/m_{min}$.

$\sqrt{A}+/\sqrt{A}-=1.1$ and thus, in a case in which a plurality of gradient index lens are present, when a ratio η of a refractive index distribution coefficient of a lens of which the refractive index distribution coefficient is a maximum to a refractive index distribution coefficient of a lens of which the refractive index distribution coefficient is a minimum is equal to or higher than 1 and equal to or lower than 1.1, a plurality of these gradient index lenses are regarded to be on the basis of the same design value.

Although an on-axis refractive index $N_{00}$ of a gradient index lens, as described in Japanese Unexamined Patent Application No. 2005-289775, ideally, is the same as the refractive index of a base material, actually, there is manufacturing error. Even in a case in which there is manufacturing error, as described in Japanese Unexamined Patent Application Publication No. 2005-289775, it can be assumed that the error is the same up to two digits after the decimal point. In other words, when there are a plurality of gradient index lenses, refractive indexes on axes of such gradient index lenses are measured, and in a case in which the refractive indexes up to two digits after the decimal point are the same, it can be regarded that the gradient index lenses are on the basis of the same design value. A measurement method of an on-axis refractive index is not particularly limited, as long as the method can measure a refractive index of a center part of a gradient index lens in the radial direction. For example, there are a critical angle method described in Japanese Unexamined Patent Application No. 2005-289775, a method using an interference microscope described in Japanese Unexamined Patent Application H8-146236, and the like. In addition, in a case in which it is difficult to perform control of an accurate measurement position, a measurement method in which, by performing measurement at a plurality of positions in a plane and selecting a largest measured value, an on-axis refractive index is determined may be also considered.

As illustrated in FIG. 5, in such a refractive index distribution having axial symmetry, a refractive index distribution $n(x, 0)$ on a zx plane and a refractive index distribution $n(0, y)$ on a yz plane are parabolic having the same shape as each other.

In such a refractive index distribution having the axial symmetry, a refractive index on the optical axis reaches a maximum, and an off-axis refractive index decreases in proportion to a square of a distance from the optical axis. In this case, as an example of a lens base material 60 that is a gradient index lens having a refractive index distribution similar to those of the first lens 6A and the second lens 6B is shown in FIG. 6, for example, an on-axis luminous flux $F_O$ diverging from an optical axis $O_{60}$ as its center progresses along an optical path of a sinusoidal wave having the optical axis as its center. Hereinafter, a length corresponding to one period of this sinusoidal wave will be referred to as a pitch length and be represented as p.

For example, an on-axis luminous flux $F_O$ diverging from a point $h_0$ on the optical axis $O_{60}$ condenses on the optical axis O at a point $h_0'$ that is separate away in the optical axis direction by p/2. The on-axis luminous flux $F_O$ condenses on the optical axis $O_{60}$ at a point $h_0''$ that is further separate away from the point $h_0'$ in the optical axis direction by p/2.

Similarly, an off-axis luminous flux $F_h$ diverging from a point of which an image height is h on the first end face 6a condenses at heights h' and h" at positions that are separate away by distances p/2 and p.

According to the lens base material 60, for example, an image of a segment $h_0h$ is formed as an inverted equal-magnification image $h_0'h'$ at a position of a distance p/2 and is formed as an erecting equal-magnification image $h_0"h"$ at a position of the distance p.

In a case in which a length of the lens base material 60 is longer than p, in accordance with repetition of similar image formation in the optical axis direction, the image of the segment $h_0h$ is transmitted. For this reason, one lens base material 60 can be used as a relay optical system.

For such a lens base material 60, as the entire length becomes longer, the number of times of image formation increases, and thus an aberration due to error of a refractive index distribution also increases.

In order to manufacture a gradient index lens, for example, a glass base material having a rod shape is formed using rod spinning, direct spinning, or the like. Thereafter, by using an ion exchange method in which a glass base material is immersed in high-temperature molten salt, a density gradient is formed in a radial direction in a component which is included in the glass base material and which contributes to a refractive index. When a density gradient varies in a manufacturing process, error occurs in the refractive index distribution.

In addition, for example, a method in which a plurality of resin layers having different refractive indexes from each other are caused to compositely spin in concentric circle shapes, and after a plastic base material having a rod shape is formed, a refractive index gradient is provided through photopolymerization is known as well. In this case, for example, error is caused in a refractive index distribution in accordance with error in the nozzle shape, a deviation in the monomer concentration gradient at the time of photopolymerization, and the like.

Figure 7:
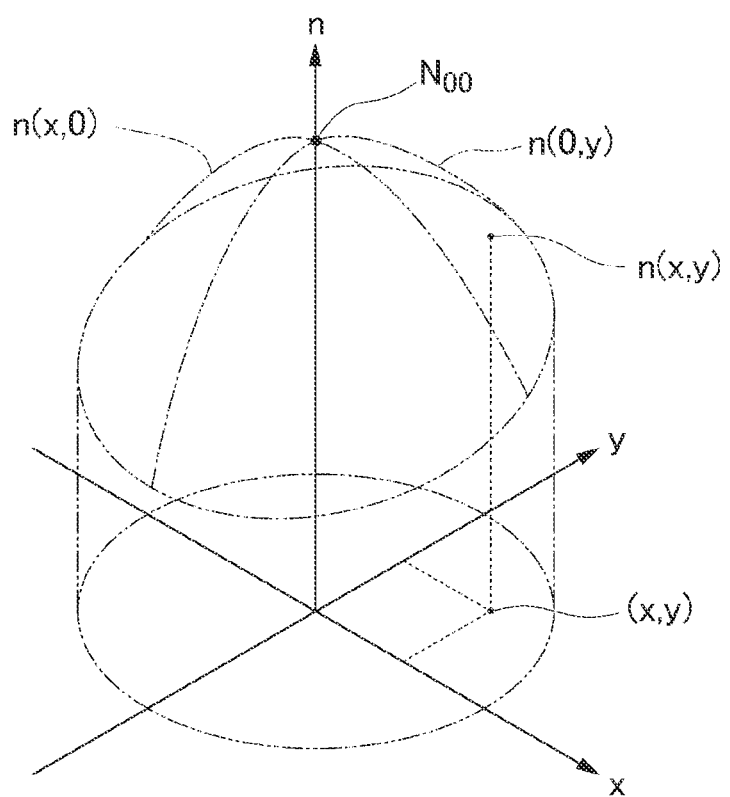
FIG. 7 is a schematic graph showing an example of a refractive index distribution including a manufacturing error in a gradient index lens.
Figure 8:
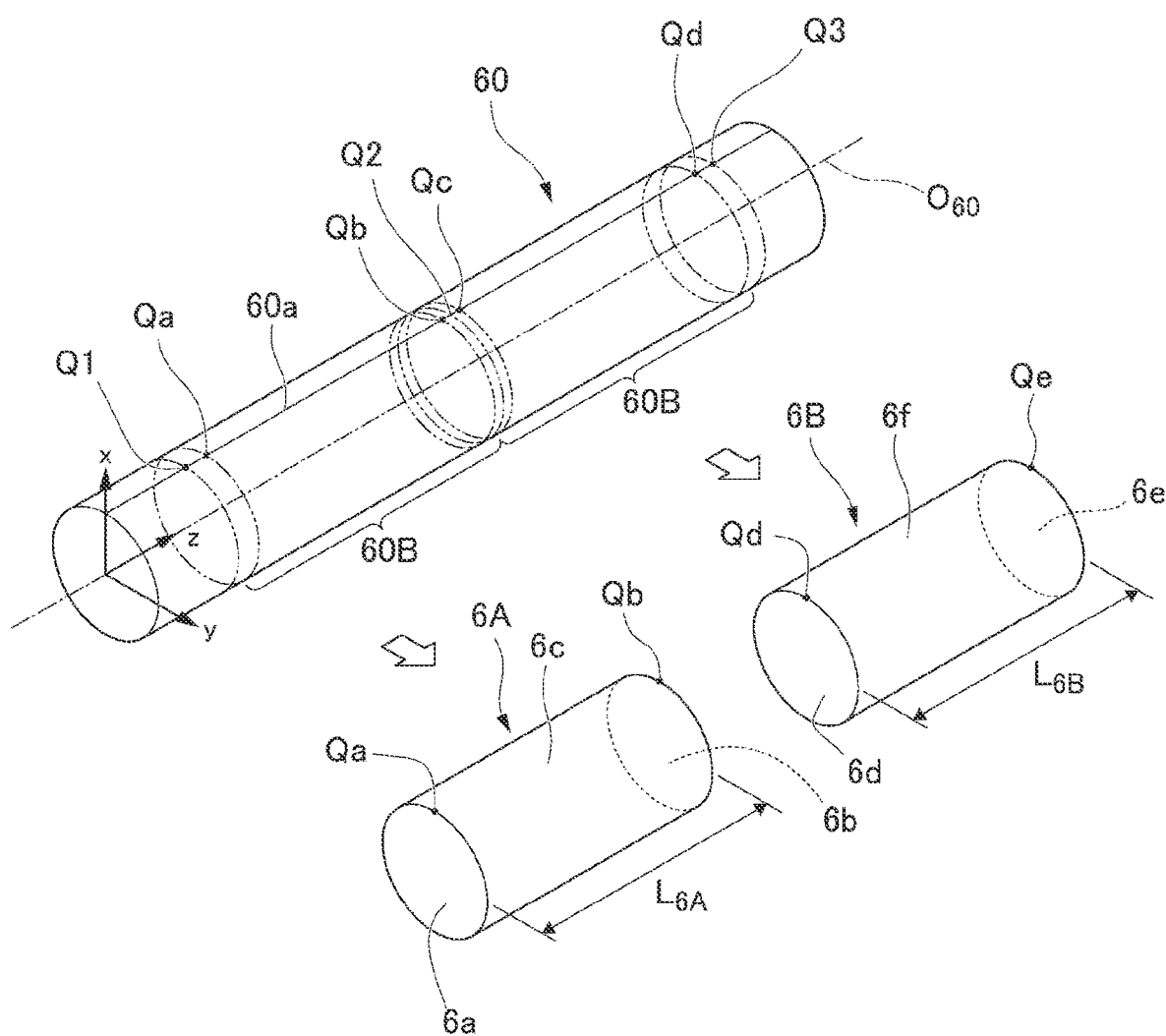
FIG. 8 is a schematic perspective view showing a relation between a plurality of lenses and a lens base material used for manufacturing these lenses in an optical system according to the first embodiment of the present invention.

FIG. 7 is a schematic graph showing an example of a refractive index distribution including a manufacturing error in a gradient index lens. The horizontal axis and the vertical axis have meanings similar to those in FIG. 5. FIG. 8 is a schematic perspective view showing a relation between a plurality of lenses and a lens base material used for manufacturing these lenses in an optical system according to the first embodiment of the present invention.

As schematically illustrated in FIG. 7, as an error in the refractive index distribution of a gradient index lens, a non-axial symmetry error is considered to frequently occur. In this case, a refractive index distribution on many cross-sections including an optical axis is a curve deviating from a target parabola. For example, it is assumed that a refractive index distribution coefficient changes in a circumferential direction around the optical axis, or a center axis of a parabola is inclined.

An inventor of the present invention has reached the present invention by considering that such an error in the refractive index distribution is assumed to be approximately constant in an area longer than a length of a lens used.

For example, as illustrated in FIG. 8, in a case in which a refractive index distribution scarcely changes in an optical axis direction in the range of a length that is in the same level as the entire length of the first lens 6A and the second lens 6B, a refractive index distribution of the first lens 6A and the second lens 6B cut out from areas of the lens base material 60 adjacent to each other in the optical axis direction is assumed to scarcely change in the optical axis direction.

The inventor of the present invention assumed that there is a high correlation between an error in the refractive index distribution and a wavefront aberration that has been transmitted through a gradient index lens and analyzed a wavefront aberration of the gradient index lens. In an analysis of a wavefront aberration, an analysis according to a wavefront aberration using a standard Zernike polynomial is effective.

First, the standard Zernike polynomial will be briefly described.

Figure 9:
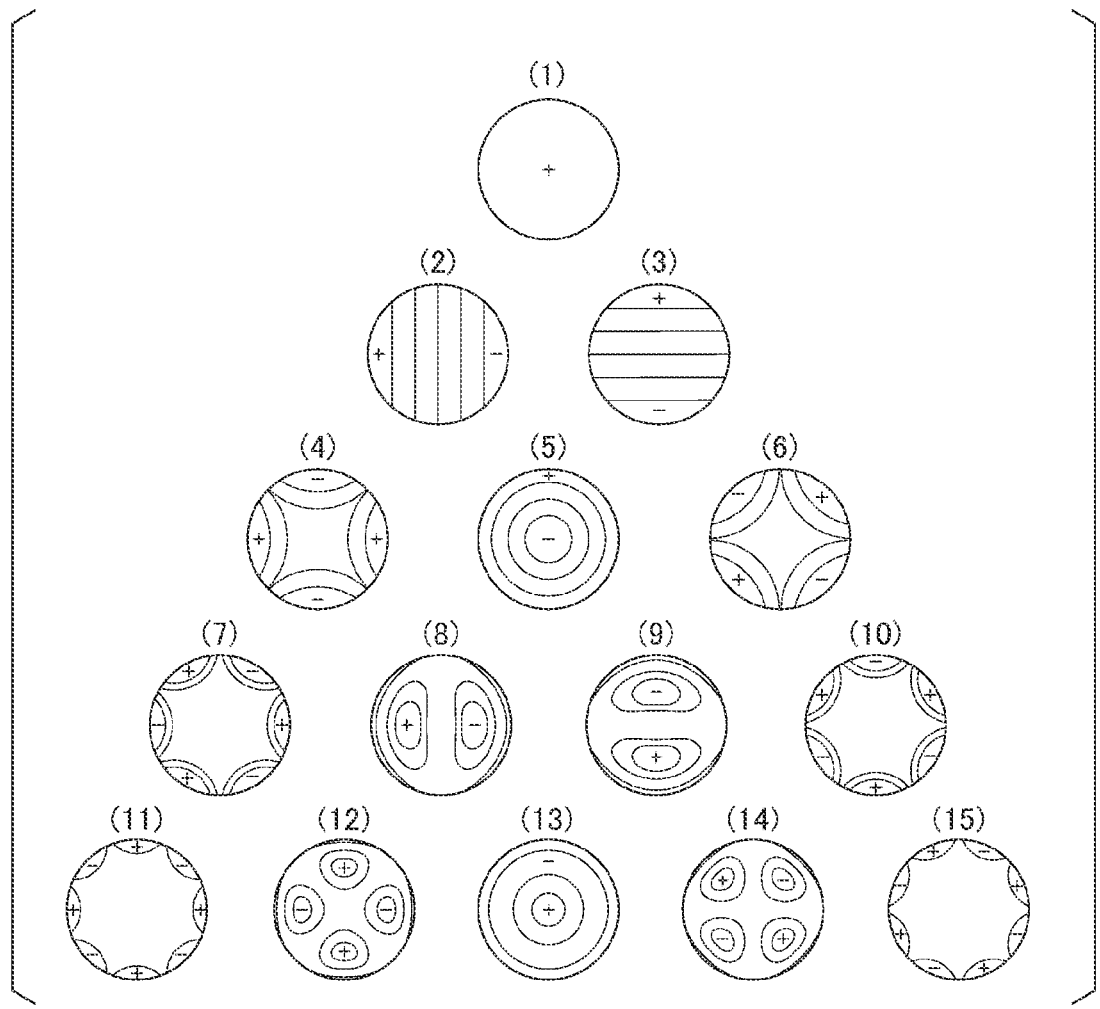
FIG. 9 is a schematic view showing a wavefront aberration represented by a standard Zernike polynomial.

FIG. 9 is a schematic view showing a wavefront aberration represented using a standard Zernike polynomial.

The standard Zernike polynomial is used as an approximation polynomial for approximating a wavefront aberration in an axis-symmetry optical system. Wavefronts represented by a standard Zernike polynomial of a 1st term to a 15th term are schematically shown in FIGS. 9(1) to 9(15). In each of the diagrams, a sign + represents to take a positive value, and a sign − represents to take a negative value. Hereinafter, an area in which the wavefront aberration takes a positive value and an area in which the wavefront aberration takes a negative value will be respectively referred to as a positive value area and a negative value area.

Hereinafter, for the simplification, unless otherwise mentioned, a standard Zernike polynomial will be simply referred to as a Zernike polynomial.

In [Table 1] represented below, $W_k(r, \theta)$ (k=1, 2, ..., 15) of a 1st term to a 15th term of the Zernike polynomial in polar coordinates are represented. Here, k represents a term number of the Zernike polynomial. (0, 0) corresponds to a position of an optical axis of the axis-symmetry optical system.

TABLE 1

| Term number k | n | m | n-2m | $W_k(r, \theta)$ | Remark |
|---|---|---|---|---|---|
| 1 | 0 | 0 | 0 | 1 | constant term |
| 2 | 1 | 0 | 1 | $r\cos\theta$ | inclination (x component) |
| 3 | 1 | 1 | −1 | $r\sin\theta$ | inclination (y component) |
| 4 | 2 | 0 | 2 | $r^2\cos 2\theta$ | Astigmatism (0 degrees direction and 90 degrees direction) |
| 5 | 2 | 1 | 0 | $2r^2 - 1$ | focus shift |
| 6 | 2 | 2 | −2 | $r^2\sin 2\theta$ | astigmatism (± 45 degrees direction) |
| 7 | 3 | 0 | 3 | $r^3\cos 3\theta$ | trefoil |
| 8 | 3 | 1 | 1 | $(3r^3 - 2r)\cos\theta$ | coma aberration of third order (x component) |
| 9 | 3 | 2 | −1 | $(3r^3 - 2r)\sin\theta$ | coma aberration of third order (y component) |
| 10 | 3 | 3 | −3 | $r^3\sin 3\theta$ | trefoil |
| 11 | 4 | 0 | 4 | $r^4\cos 4\theta$ | quadra foil |
| 12 | 4 | 1 | 2 | $(4r^4 - 3r^2)\cos 2\theta$ | secondary astigmatism |
| 13 | 4 | 2 | 0 | $6r^4 - 6r^2 + 1$ | spherical aberration of third order |
| 14 | 4 | 3 | −2 | $(4r^4 - 3r^2)\sin 2\theta$ | secondary astigmatism |
| 15 | 4 | 4 | −4 | $r^4\sin 4\theta$ | quadra foil |

A wavefront represented by the Zernike polynomial has axial symmetry with respect to the optical axis or rotation symmetry of N times (here, N is a natural number, hereinafter the same). As examples of a wavefront having axial symmetry, there are k=1, 5, and 13 (see FIGS. 9(1), 9(5), and 9(13)). A wavefront of k=13 represents a spherical aberration of a third order.

The rotation symmetry of N times in the Zernike polynomial is due to a function of θ configured with a sin(Nθ) or cos(Nθ) function and thus has a property of a sum of a wavefront of the rotation symmetry of N times and a wavefront acquired by rotating this wavefront by (2M+1)×

(360/2N) degrees around the optical axis (here, M is an integer) being 0 all over the place.

As examples of N=1, there are k=2, 3, 8, and 9 (see FIGS. 9(2), 9(3), 9(8), and 9(9)). Wavefronts of k=2 and 3 represent wavefronts inclined in the x direction and the y direction. Wavefronts of k=8 and 9 represent coma aberrations of the third order in the x direction and the v direction.

As examples of N=2, there are k=4, 6, 12, and 14 (see FIGS. 9(2), 9(3), 9(12), and 9(14)). Wavefronts of k=4 and 6 represent astigmatisms in the directions of 0 degrees and 90 degrees and the directions of ±45 degrees. Wavefronts of k=12 and 14 represent secondary astigmatisms.

As examples of N=3, there are k=7 and 10 (see FIGS. 9(7) and 9(10)). Wavefronts of k=7 and 10 represent trefoils.

As examples of N=4, there are k=11 and 15 (see FIGS. 9(11) and 9(15)). Wavefronts of k=11 and 15 represent quadra foils.

In approximating a transmission wavefront aberration $W(r, \theta)$ of a gradient index lens by a Zernike polynomial, as represented in the following Equation (c), $W(r, \theta)$ is represented as linear combination of a 1st term to a K-th term (here, K is a natural number) of the Zernike polynomial, and, for example, coefficients $a_k$ (here, k=1, . . . , K) of $W_k(r, \theta)$ are determined using a least squares method or the like. Hereinafter, the coefficient $a_k$ will be referred to as a Zernike coefficient.

$$W(r, \theta) = \sum_{k=1}^{K} a_k W_k(r, \theta) \quad \text{(c)}$$

Figure 10:
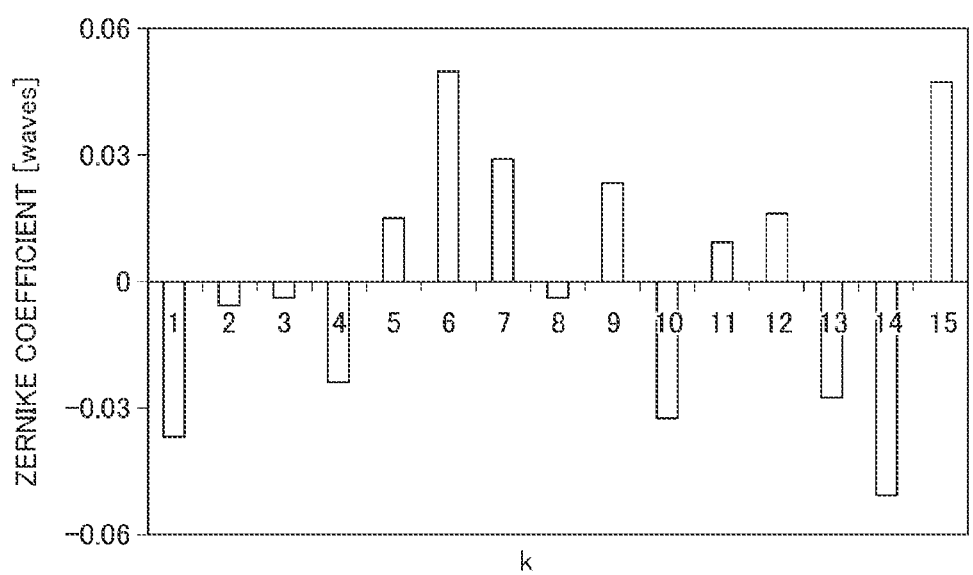
FIG. 10 is a schematic bar graph showing an example of Zernike coefficients representing a wavefront aberration of a gradient index lens.

FIG. 10 is a schematic bar graph showing an example of a Zernike coefficient representing a wavefront aberration of a gradient index lens. In FIG. 10, the horizontal axis represents a term number k, and the vertical axis represents the magnitude of a Zernike coefficient $a_k$ [waves].

FIG. 10 shows measurement results of wavefront aberrations of a gradient index lens which is available, of which an outer diameter D is 0.35 mm, a length L is 60 mm, and the number of times of image formation is 8 times. As a measurement luminous flux, an on-axis luminous flux was used. As a measurement device, a Shack-Hartmann sensor was used.

According to this measurement example, although axis-symmetry aberration components such as a13 corresponding to a spherical aberration and the like are also included, for example, it can be understood that many non-axial symmetry aberration components such as astigmatisms ($a_4$, $a_6$), trefoils ($a_7$, $a_{10}$), and coma aberrations ($a_8$, $a_9$) are included.

According to a review of the inventor of the present invention, non-axial symmetry aberration components are included in a wavefront aberration of a gradient index lens in greater or lesser degrees.

The inventor has reached the present invention by finding that aberration components of non-axial symmetry can be reduced by cutting out a gradient index lens into a plurality of gradient index lenses and adjusting a relative rotation position of the plurality of gradient index lenses.

A detailed configuration of the first lens 6A and the second lens 6B of the gradient index lens group 6 according to this embodiment will be described together with a manufacturing method according to this embodiment.

As shown in FIG. 8, a first lens 6A and a second lens 6B are cut out from a lens base material 60. Hereinafter, a position in an optical axis direction in the lens base material 60 is represented as a point on a straight line 60a formed in accordance with an outer peripheral face of the lens base material 60 and a positive value area of the x axis intersecting each other.

The first lens 6A is manufactured by polishing both end parts of a cut piece 60A in a longitudinal direction that is cut out at positions of a point Q1 and a point Q2. For this reason, a length of a segment Q1Q2 is longer than $L_{6A}$.

In the first lens 6A, intersections between outer edges of a first end face 6a and a second end face 6b and the straight line 60a are represented as points Qa and Qb.

The second lens 6B is cut out from the lens base material 60 adjacent to a cut piece 60B. For example, the cut piece 60B is cut out at positions of points Q2 and Q3. Here, a length of a segment Q2Q3 is longer than $L_{6B}$. The second lens 6B is manufactured by polishing both end parts of the cut piece 60B in the longitudinal direction.

In the second lens 6B, intersections between outer edges of a first end face 6d and a second end face 6e and the straight line 60a are represented as points Qd and Qe.

Figure 11:
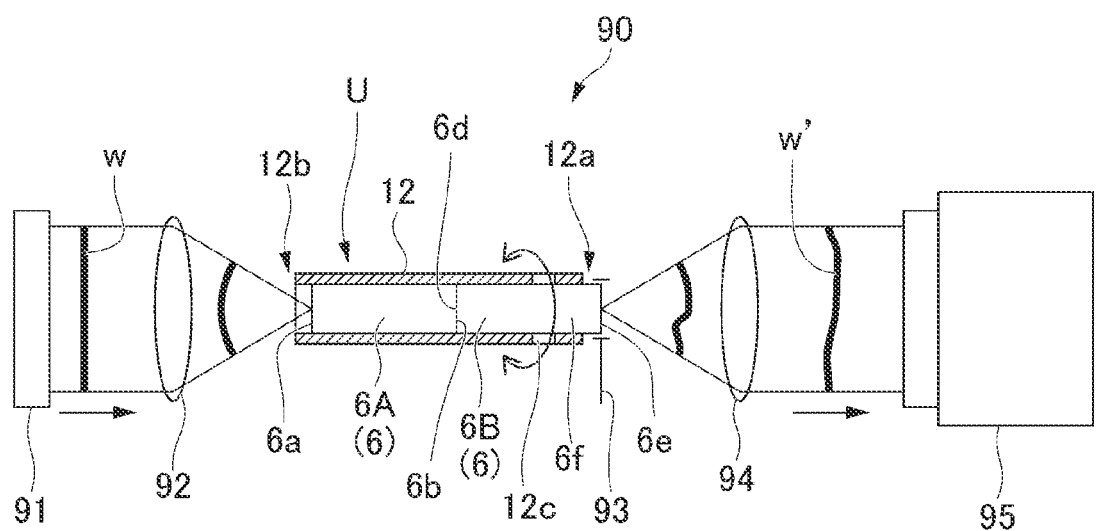
FIG. 11 is a schematic view showing an example of a method for manufacturing an optical system according to the first embodiment of the present invention.
Figure 12:
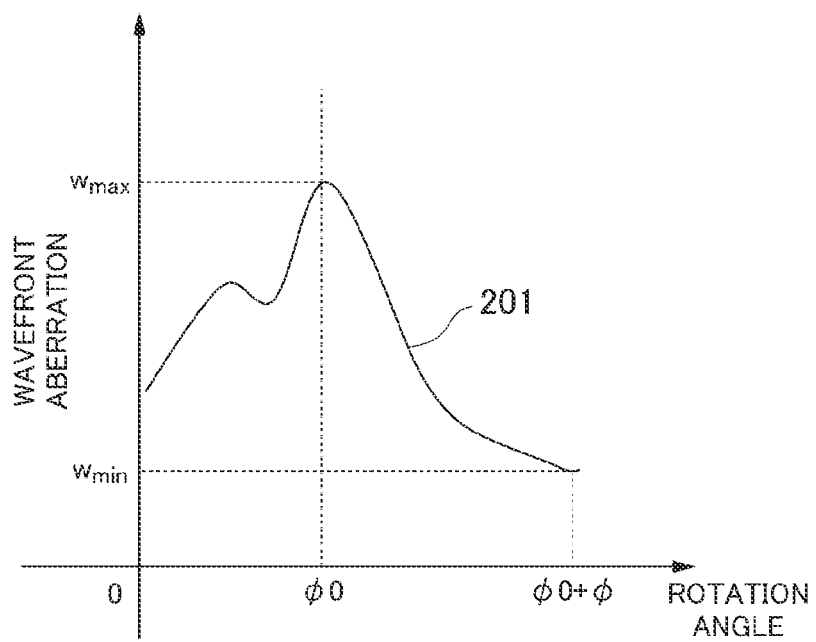
FIG. 12 is a schematic view showing an example of a change in a wavefront aberration in the method for manufacturing an optical system according to the first embodiment of the present invention.
Figure 13:
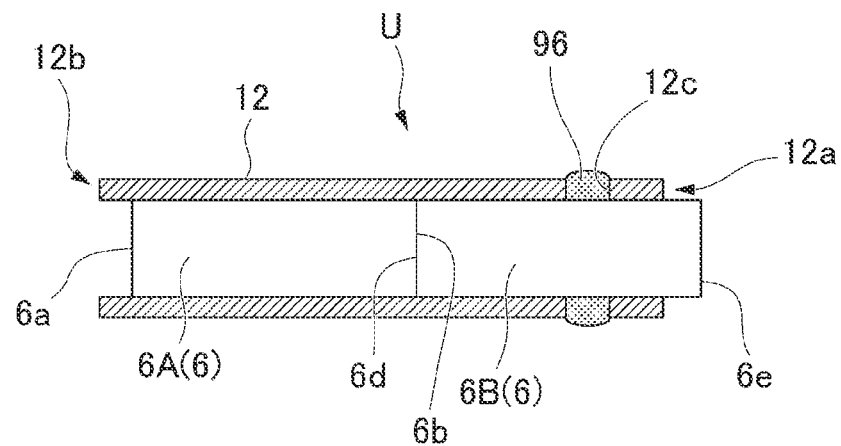
FIG. 13 is a schematic view showing an example of the method for manufacturing an optical system according to the first embodiment of the present invention.

FIG. 11 is a schematic view showing an example of a method for manufacturing an optical system according to the first embodiment of the present invention. FIG. 12 is a schematic view showing an example of a change in a wavefront aberration in the method for manufacturing an optical system according to the first embodiment of the present invention. FIG. 13 is a schematic view showing an example of the method for manufacturing an optical system according to the first embodiment of the present invention.

After the first lens 6A and the second lens 6B are cut out from the lens base material 60, as shown in FIG. 11, the first lens 6A is fixed to the inside of the inner cylinder 12 in a posture in which the first end face 6a is turned to a side of the second end part 12b. Between the first end face 6a and the second end part 12b, a space in which an objective optical system 5 not shown is disposed is formed.

A method for fixing the first lens 6A is not particularly limited. For example, the first lens 6A may be bonded to the inner cylinder 12.

The second lens 6B is inserted into the inside of the inner cylinder 12 between the first end face 6a and the second end part 12b. In this embodiment, the second end face 6e protrudes to the outer side from the first end part 12a in a state in which the first end face 6d of the second lens 6B is brought into contact with the second end face 6b.

An adhesive fixing part 12c for bonding the second lens 6B is provided in the inner cylinder 12. In the example shown in FIG. 11, the adhesive fixing part 12c is formed from a through hole that passes through a side face of the inner cylinder 12 and faces the outer peripheral face 6f Here, for example, by fixing the first end part 12a of the inner cylinder 12 and the outer peripheral face 6f using an adhesive, the first end part 12a may be configured to function also as an adhesive fixing part. In such a case, the adhesive fixing part 12c is unnecessary.

An assembly U of the inner cylinder 12, the first lens 6A, and the second lens 6B configured in this way is held in a holding part, which is not shown, of an adjustment jig 90.

The adjustment jig 90 includes a light source part 91, a first condensing lens 92, a lens rotating part 93, a second condensing lens 94, and a wavefront measuring device 95.

The light source part 91 forms planar waves that are used as luminous fluxes for measurement. The first condensing lens 92 condenses luminous fluxes for measurement on the first end face 6a. The lens rotating part 93 holds an end part of the second lens 6B near the second end face 6e and rotates the second lens 6B around the optical axis. The second condensing lens 94 converts light output from the second end face 6e into parallel luminous fluxes.

The wavefront measuring device 95 measures a wavefront of the parallel luminous fluxes from the second condensing lens 94. The wavefront measuring device 95 is not particularly limited as long as it is able to measure a total amount of wavefront aberrations.

Thereafter, while the second lens 6B is rotated around the optical axis using the lens rotating part 93, the wavefront aberration of the optical system configured of the first lens 6A and the second lens 6B is measured using the wavefront measuring device 95. The luminous fluxes for measurement do not have any wavefront aberration and thus the wavefront W is a plane surface. On the other hand, in a wavefront W of luminous fluxes incident in the wavefront measuring device 95, wavefront aberrations of the optical system generated from the first lens 6A and the second lens 6B are superimposed.

The first lens 6A and the second lens 6B have non-axial symmetry aberrations similar to each other. In a state in which the points Qa and Qb are positioned on the same lines as each other and the points Qd and Qe are positioned on the same lines as each other, the first lens 6A and the second lens 6B have completely the same optical performance as that of the lens base material 60 of a length L. For this reason, a total wavefront aberration of the first lens 6A and the second lens 6B is equal to the wavefront aberration of the lens base material 60.

On the other hand, for example, in a case in which the point Qa (Qb) and the point Qd (Qe) deviate from each other around the optical axis, a positive value area and a negative value area of each non-axial symmetry wavefront overlap each other in accordance with an amount of relative rotation, whereby at least of part of the non-axial symmetry aberration is reduced.

FIG. 12 shows an example of a change in the aberration amount with a rotation angle of the second lens 6B of the assembly U set as a horizontal axis and an amount of the wavefront aberration set as a vertical axis. In the example shown in FIG. 12, when the rotation angle changes from φ0 to φ0+φ, the amount of the aberration changes from a maximum value $w_{max}$ to a minimum value $w_{min}$ (here, $w_{min} < w_{max}$). Here, except for a specific case to be described below, a state in which the maximum value $w_{max}$ is taken corresponds to a state in which positions of the point Qa (Qb) and the point Qd (Qe) around the optical axis coincide with each other (the relative rotation angle is 0 degrees).

A rotation angle φ0 represents a rotation position at which a total aberration of the first lens 6A and the second lens 6B reaches a maximum and will be referred to as a reference rotation position. On the other hand, φ represents a rotation angle using the reference rotation position as a reference. φ is represented by a numerical value in the range of 0 degrees to 360 degrees with the rotation direction fixed to one direction. In this case, φ constantly takes a positive value and thus represents the magnitude thereof.

Furthermore, in the case of this embodiment, φ also represents a mutual relative rotation angle of the first lens 6A and the second lens 6B that are two lenses in the gradient index lens group 6. For this reason, hereinafter, the rotation angle φ will be referred to as a relative rotation angle φ.

Here, a relation between an effect of an aberration reduction and a lens length will be considered. For the simplification of description, a case in which the lens base material 60 has only an aberration of an 8th term (see FIG. 9(8)) will be considered. This aberration has one-time rotation symmetry and thus, when a relative rotation angle φ of the second lens 6B with respect to the first lens 6A is 180 degrees, a maximum effect of aberration reduction can be acquired.

In a case in which the refractive index distribution of a gradient index lens does not change with respect to the optical axis direction, the aberration amount is in proportion to the length of the gradient index lens. For example, when the aberration amount per unit length is $b_8$, the aberration amount $w_{60}$ of the lens base material 60 of the length L is represented in the following Equation (d), and the aberration amounts $w_{6A}$ and $w_{6B}$ of the first lens 6A and the second lens 6B as single bodies are represented in the following Equations (e) and (f).

$$w_{60} = b_8 L \tag{d}$$

$$w_{6A} = b_8 L_{6A} \tag{e}$$

$$w_{6B} = b_8 L_{6B} \tag{e}$$

When an aberration amount in a case in which the relative rotation angle φ is 180 degrees (=π) is $w_\pi$, the second lens 6B is located at a position in which the aberration of the second lens 6B offsets the aberration of the first lens 6A, and thus it can be represented as in the following Equations (g-1) and (g-2).

$$w_\pi = b_8(L_{6A} - L_{6B}) \tag{g-1}$$

$$w_\pi = b_8 L\left(1 - 2\frac{L_{6B}}{L}\right) \tag{g-2}$$

Here, from an Equation (g-1), in case of $L_{6A}=L_{6B}$, $w_\pi$ is 0. However, as can be understood from an Equation (g-2), it can be understood that, even when $L_{6A} \neq L_{6B}$, $w_\pi$ is smaller than $w_{60}$.

As an aberration amount $w_{<\pi}$ of a case in which the relative rotation angle is smaller than 180 degrees, a similar result expect for the minimum value being larger than 0 is acquired.

In this way, in a case in which the first lens 6A and the second lens 6B of which a total length is L are formed from the lens base material 60 and are relatively rotated around the optical axis, a ratio between lengths $L_{6A}$ and $L_{6B}$ of the first lens 6A and the second lens 6B is not particularly limited, and the lengths $L_{6A}$ and $L_{6B}$ are more preferable to be a length of L/2 or a length close to L/2.

In a case in which the gradient index lens group 6 configured by forming three or more lenses from the lens base material 60 such that a total length becomes L, the description presented above can be applied also between arbitrary two lenses among the lenses. In this case, except for a case in which all the lenses are aligned at a reference rotation position, the aberration amount is smaller than that of one gradient index lens of a length of L formed from the lens base material 60.

As a result of the review of the inventor of the present invention, it can be understood that, in a case in which a deviation of a specific refractive index distribution or an aberration of a specific term of a lens base material of a specific total length L is to be reduced in the rotation adjustment described above, there are also cases in which a state in which the maximum value $w_{max}$ is taken does not correspond to a state in which the positions of the point Qa (Qb) and the point Qd (Qe) around the optical axis do not coincide with each other (a relative rotation angle is 0 degrees).

However, even in such cases, when a pitch P of the lens base material satisfies the following Equation (12), it can be understood that the state in which the maximum value $w_{max}$ is taken and the state in which the relative rotation angle is 0 degrees described above can be made correspond to each other. Thus, it is more preferable that the pitch P of the lens base material satisfy the following Equation (12).

$$2n+0.25<P<2n+0.75 \tag{12}$$

Here, n is an integer equal to or greater than 0.

The pitch P of the lens base material may be designed such that it satisfies Equation (12) or may be designed to have a size not satisfying Equation (12) described above.

In a case in which the pitch P of the lens base material does not satisfy Equation (12), the lens base material may be divided into a plurality of lens base materials satisfying Equation (12), and then the rotation adjustment described above may be performed for each of the lens base materials.

The rotation adjustment described above is repeated until a convergence determination condition determined in advance is satisfied. As the convergence determination condition, for example, there is a condition of [A] the aberration amount being a minimum value, [B] the aberration amount being equal to or smaller than a target value determined in advance, or the like.

For example, in a case in which the convergence determination condition is [A], when the aberration amount is the minimum value $w_{min}$, the driving of the lens rotating part 93 is stopped.

In this state, the second lens 6B is fixed to the inner cylinder 12. For example, as shown in FIG. 13, by coating the adhesive fixing part 12c with an adhesive 96 and then curing the adhesive 96, the second lens 6B and the inner cylinder 12 are bonded to each other. As the curing method, a curing method that is appropriate in accordance with a type of the adhesive 96 is used.

For example, in a case in which the adhesive 96 is a UV curing-type adhesive, the adhesive 96 can be cured by performing the rotation adjustment described above in a state in which the adhesive fixing part 12c is coated with the adhesive 96 in advance and thereafter irradiating UV light to the adhesive 96.

In this way, the first lens 6A and the second lens 6B are fixed to the inner cylinder 12. In such a fixed state, as shown in FIG. 3, when a point Qa of the first lens 6A is on the x axis, as shown in FIG. 4, a point Qd of the second lens 6B is disposed at a position that is relatively rotated around the optical axis O as its center by φ in a clockwise direction from the x axis to the y axis.

As will be described below, the relative rotation angle φ of the second lens 6B is different in accordance with kinds of non-axial symmetry and aberrations of the first lens 6A and the second lens 6B and aberration amounts thereof.

Thereafter, the objective optical system 5 is disposed inside the assembly U. and the objective optical system 5 is fixed to the inner cylinder 12. In addition, the fixed inner cylinder 12 to which the gradient index lens group 6 and the objective optical system 5 are bonded is fixed to the inside of the outer cylinder 11. At this time, as is necessary, a relative position between the focusing optical system 7 and the gradient index lens group 6 disposed inside the casing 2 is adjusted.

In this way, an endoscope 100 having an optical system configured with the objective optical system 5, the gradient index lens group 6, and the imaging optical system 7 is manufactured.

As described above, in the optical system according to this embodiment, the first lens 6A and the second lens 6B having the same refractive index distribution are disposed on the same axis as each other, and a relative rotation angle φ around an optical axis is adjusted such that the wavefront aberration is a minimum. In such an optical system formed from the first lens 6A and the second lens 6B, the aberration amount is smaller than that of one gradient index lens of a length of L cut out from the lens base material 60 having the same refractive index distribution as the first and second lenses 6A, 6B. In other words, without reducing the aberration amount by increasing accuracy of the distribution of the gradient index lens or correcting the aberration of the gradient index lens using another optical element, the aberration amount of the entire optical system configured with the first lens 6A and the second lens 6B is reduced.

In accordance with this, in a case in which the aberrations of the objective optical system 5 and the imaging optical system 7 are constant, the aberration of the optical system is reduced. As a result, deterioration of the quality of an image transmitted by the optical system is reduced.

In addition, if there is a relative rotation angle φ at which the aberration of the entire system including the objective optical system 5 and the imaging optical system 7 is reduced, adjustment to such a relative angle may be performed.

By considering that the aberration amount of a gradient index lens increases in accordance with an increase in the length thereof, the effect of the configuration according to this embodiment described above becomes more remarkable as the length L of the gradient index lens group 6 becomes longer.

As disclosed in Japanese Unexamined Patent Application Publication No. 2007-176764 and the like, a refractive index can be measured with high accuracy up to 5 digits after the decimal point. Under such measurement accuracy, the manufacturing accuracy of a refractive index distribution is about $5 \times 10^{-6}$ in terms of an error in the refractive index value. Thus, the magnitude Δn of the manufacturing error of the refractive index distribution can be estimated as being $5 \times 10^{-6}$.

An aberration of one gradient index lens is an error in the length of an optical path due to an error in the refractive index, and thus when the length of the gradient index lens is L', the aberration amount is about Δn×L'.

Meanwhile, as a criterion for reach of an optical system at a refraction limit, there is a condition of a PV value of the wavefront aberration being equal to or smaller than 0.25λ in which a designed wavelength is λ.

Thus, a usable length L' as one gradient index lens can be estimated as being L'≤0.25 λ/Δn.

Thus, the image quality can be improved more remarkably than one gradient index lens having the same refractive index distribution, and thus it is more preferable that the entire length L of the gradient index lens group 6 be larger than a maximum value of L'.

In other words, it is more preferable that the gradient index lens group 6 satisfy the following Equation (h).

$$L > \frac{0.25\lambda}{\Delta n} \tag{h}$$

In the gradient index lens group 6. Equation (i) is satisfied as below, and thus by using this, Equation (h) can be transformed into Equation (j) as below.

$$L > \frac{D \times N_{00} \times \pi \times P}{NA} \quad \text{(i)}$$

$$P > \frac{0.25\lambda \times NA}{\Delta n \times D \times N_{00} \times \pi} \quad \text{(j)}$$

Here, P is a total pitch of the gradient index lens group 6, and NA is the numerical aperture on the axis of the gradient index lens group 6. $N_{00}$ and D are respectively an on-axis refractive index and an outer diameter of the gradient index lens group 6.

The total pitch P represents a ratio acquired by dividing the entire length L of the gradient index lens group 6 by a length corresponding to one period of on-axis luminous fluxes progressing in a sinusoidal wave pattern inside the gradient index lens group 6.

In Equation (j), when $\Delta n$ is substituted with $5 \times 10^{-6}$, and [nm] and [mm] are respectively used as units of $\lambda$ and D, the following Equation (1) can be acquired. It is more preferable that the gradient index lens group 6 satisfy the following Equation (1).

$$P > \frac{0.25\lambda \times NA}{5 \times D \times N_{00} \times \pi} \quad \text{(1)}$$

Next, conditions of a plurality of lenses configuring the gradient index lens group 6 in a case in which the PV value of the wavefront aberration is set to be equal to or smaller than $0.25\lambda$ will be described.

As described above, when the length of a lens relatively rotating in a gradient index lens is too short, there is concern that the aberration amount cannot be sufficiently reduced. When a total pitch of the gradient index lens group 6 is P, and a pitch of a lens shortest in the gradient index lens group 6 is $P_S$, similar to Equations (g-1) and (g-2), the aberration $L\Delta n$ of the entirety at a reference rotation position is represented by the following Equation (k).

$$w_r = (1 - 2\gamma)L\Delta n \quad \text{(k)}$$

$$\gamma = \frac{P_S}{P} \quad \text{(m)}$$

Since $\gamma > 0$, from Equation (k), $w_r < L\Delta n$.

When Equation (i) is substituted with Equation (k), a condition for $w_r$ being smaller than $0.25\lambda$ can be represented as in the following Equation (p).

$$\gamma > \frac{1}{2} - \frac{0.25\lambda \times NA}{2 \times \Delta n \times D \times N_{00} \times \pi \times P} \quad \text{(p)}$$

When $\Delta n$ is substituted with $5 \times 10^{-6}$ in Equation (p), and [nm] and [mm] are respectively used as units of $\lambda$ and D, the following Equation (2) can be acquired. It is more preferable that the gradient index lens group 6 satisfy the following Equation (2).

$$\gamma > 0.5 - \frac{0.25\lambda \times NA}{10\pi \times P \times D \times N_{00}} \quad \text{(2)}$$

Furthermore, it is more preferable that a pitch $P_S$ of a lens of which pitch is the shortest in the gradient index lens group 6 is equal to or larger than 0.5. When this condition is satisfied, at least one real image is formed in each lens in the gradient index lens group 6, and thus the number of times of relay of a real image increases in the gradient index lens group 6 as a whole.

In a case in which rotation adjustment is not performed, the aberration increases in accordance with the number of times of relay. However, according to the method for manufacturing an optical system of this embodiment, such an aberration can be reduced, and thus the effect of reduction of the aberration becomes larger as the number of times of relay increases.

Second Embodiment

A method for manufacturing an optical system according to a second embodiment of the present invention will be described.

Figure 14:
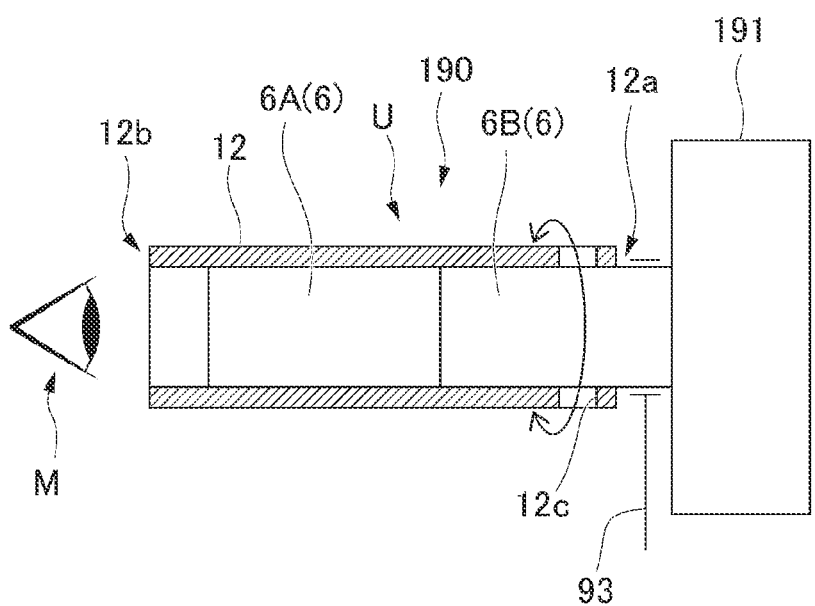
FIG. 14 is a schematic view showing an example of a method for manufacturing an optical system according to a second embodiment of the present invention.

FIG. 14 is a schematic view showing an example of the method for manufacturing an optical system according to the second embodiment of the present invention.

The manufacturing method according to this embodiment is different from the first embodiment in a method for adjusting a gradient index lens group 6 in an optical system used in an endoscope 100. Hereinafter, points different from the first embodiment will be focused on in description.

As illustrated in FIG. 14, in the manufacturing method according to this embodiment, an adjustment jig 190 is used in place of the adjustment jig 90. In the adjustment jig 190, an optical chart 191 (an image evaluation chart) is used in place of the wavefront measuring device 95. As the optical chart 191, an appropriate chart that can be used for evaluating an optical performance relating to an aberration of a gradient index lens group 6 is used. For example, as the optical chart 191, a resolving power chart, a line chart, a dot chart, or the like may be used. For example, visibility may be adjusted by using a biological organization or an industrial product that is an observation target of the gradient index lens group 6 as an image evaluation chart.

In the example shown in FIG. 14, the optical chart 191 is disposed on an object plane of the gradient index lens group 6, and a measurer M visually observes an image of the optical chart 191 through the optical system of the gradient index lens group 6. Here, between the optical chart 191 and a second lens 6B and between a first lens 6A and the measurer M, an objective optical system and an imaging optical system that are appropriate for image observation may be provided. However, visual observation of the chart is not limited to such direct visual observation and visual observation through an optical system for image observation. For example, the measurer M may visually see an image of a chart output using an image acquiring element such as an imaging element or the like.

The measurer M adjusts a rotation position of the second lens 6B such that the optical chart 191 is seen the most clearly by rotating the second lens 6B by operating a lens rotating part 93.

At that time, in order to easily notice a change in the sharpness of an image, it is more preferable that the measurer M observe the optical chart 191 while the second lens 6B is rotated. However, the measurer M may observe the optical chart 191 before rotation and after rotation of the second lens 6B.

When the adjustment of the rotation position of the second lens 6B ends, similar to the first embodiment, the second lens 6B is fixed to the inner cylinder 12. In addition, similar to the first embodiment, an endoscope 100 is manufactured.

In this way, according to this embodiment, the rotation adjustment of the second lens 6B is performed through visual observation. According to this embodiment, without using the expensive wavefront measuring device 95 or the like, the rotation adjustment of the second lens 6B can be performed.

In an optical system manufactured using the manufacturing method according to this embodiment, similar to the first embodiment, without reducing the aberration amount of the gradient index lens, deterioration of the image quality can be reduced.

Third Embodiment

A method for manufacturing an optical system according to a third embodiment of the present invention will be described.

Figure 15:
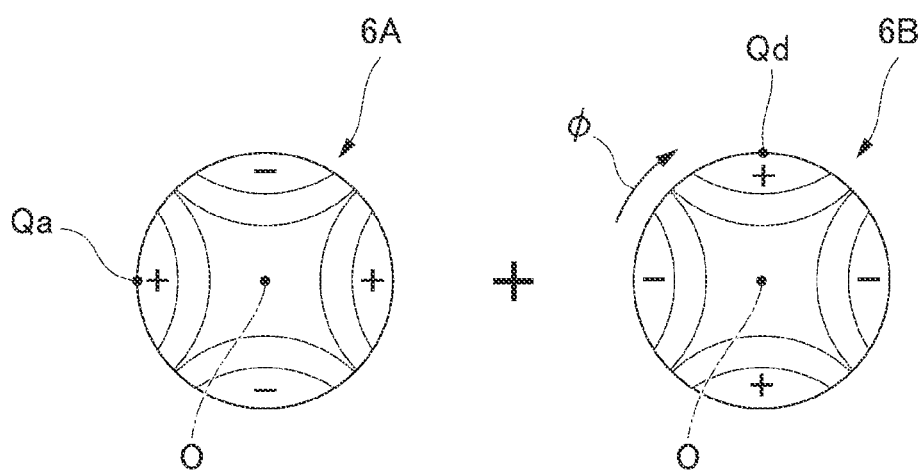
FIG. 15 is a schematic view showing a principle of a method for manufacturing an optical system according to a third embodiment of the present invention.

FIG. 15 is a schematic view showing a principle of the method for manufacturing an optical system according to the third embodiment of the present invention.

In this embodiment, the method for manufacturing a gradient index lens group 6 in an optical system used for an endoscope 100 is different from that according to the first embodiment. Hereinafter, points different from the first embodiment will be focused on in description.

In the manufacturing method according to this embodiment, an aberration amount for each type of aberration of a lens base material 60 is measured in advance, and a relative rotation angle φ of a second lens 6B is determined in accordance with the aberration amount.

Measurement of an aberration of the lens base material 60 is performed using a gradient index distribution lens acquired by cutting out a part of an appropriate length from the lens base material 60. The measurement of the aberration of the lens base material 60 may be performed using a first lens 6A or the second lens 6B.

The measurement of an aberration of the lens base material 60, for example, may be performed using a Shack Hartman sensor or the like.

The measurement of an aberration of the lens base material 60 may be performed at least once for a range of a length of the lens base material 60 in which a refractive index distribution is almost constant. For example, the measurement of an aberration of the lens base material 60 may be performed at least once for each manufacturing lot of the lens base material 60.

In a case in which the first lens 6A and the second lens 6B have aberrations of N-times rotation symmetry, when a relative rotation angle φ is set to $(2M+1)\times(360/2N)$ degrees (here, N is a natural number), the aberration of the entire gradient index lens group 6 is reduced. Particularly, in a case in which $L_{6A}=L_{6B}$, the aberrations of the N-times rotation symmetry offset each other.

In a case in which there are a plurality of N in the aberrations of the N-times rotation symmetry, it is more preferable that a relative rotation angle φ for reducing N of which the aberration amount is large be selected.

For example, as shown in FIG. 15, in a case in which an astigmatism of which a term number k of the Zernike polynomial is 4 is distinguished in the aberration of the lens base material 60, an aberration of which a term number k has 2-times rotation symmetry, and thus an optimal value of relative rotation angle φ of the second lens 6B is an odd number times of 90 degrees. In the case of such a relative rotation angle q, a positive value area and a negative value area of the wavefront overlap each other, and thus the astigmatism is reduced.

In a case in which there are a plurality of types of aberrations having N-times rotation symmetry (here, N is constant) in aberrations of the lens base material 60, aberration amounts according to the types of the aberrations are similarly reduced in accordance with relative rotation of a relative rotation angle φ.

For example, as another example of types of aberration of N=2, there are aberrations of which term numbers k are 6, 12, 14, and the like. In this case, by setting the relative rotation angle φ to odd-number times of 90 degrees, aberrations corresponding to term numbers k are reduced with the same degree.

Here, a result of a numerical simulation of a reduction amount of the aberration amount according to the relative rotation angle φ will be described.

Figure 16:
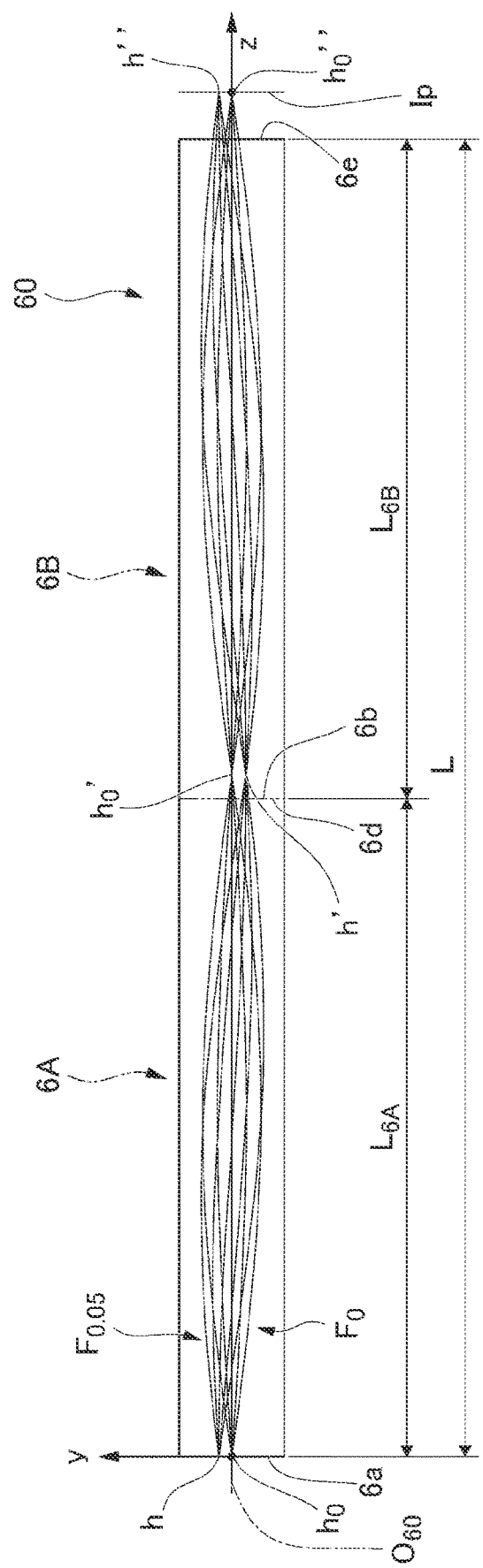
FIG. 16 is a ray tracing diagram showing an example of ray tracing in a gradient index lens having an error in a refractive index distribution.
Figure 17:
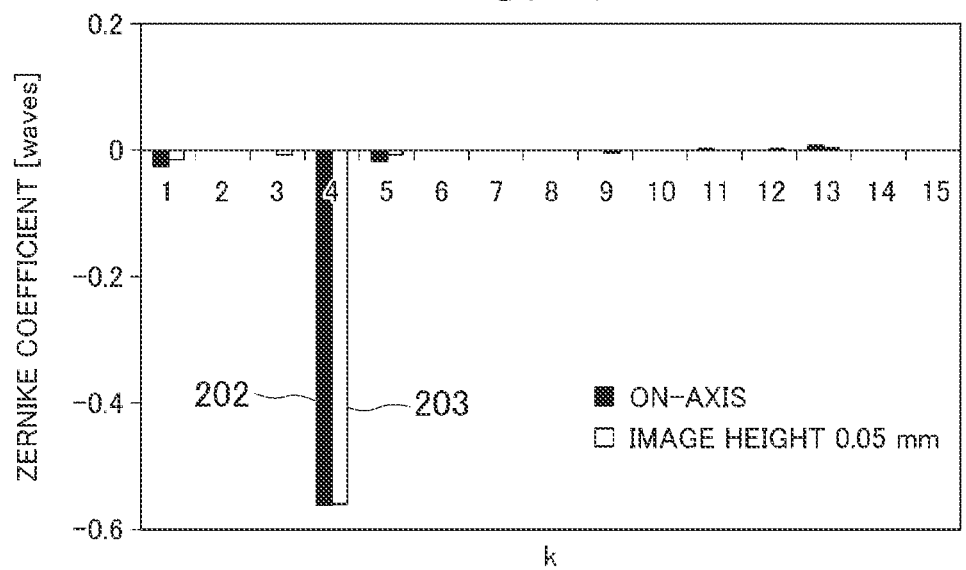
FIG. 17 is a schematic bar graph showing an example of a Zernike coefficient representing a wavefront aberration of a gradient index lens.
Figure 18:
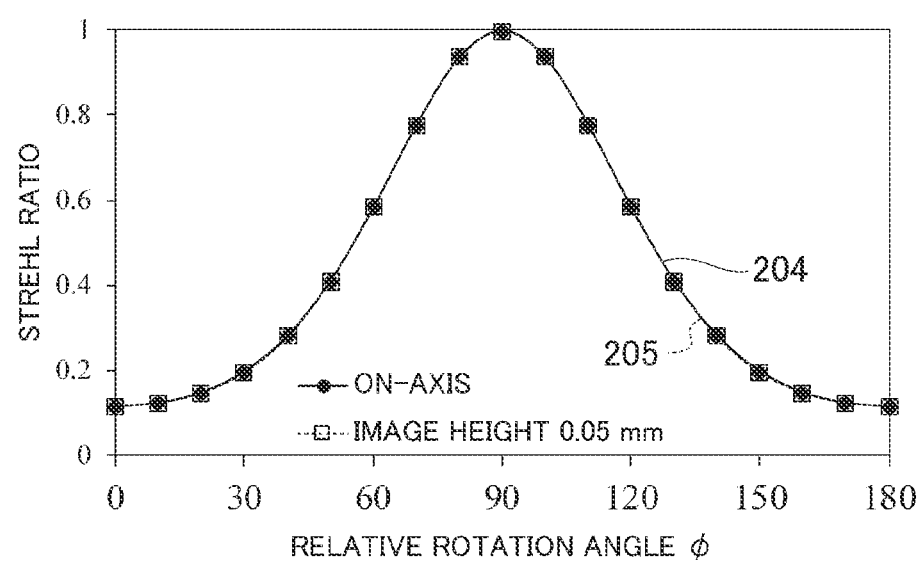
FIG. 18 is a schematic graph showing a reaction of a method for manufacturing an optical system according to the third embodiment of the present invention.

FIG. 16 is a light ray tracing diagram showing an example of ray tracing in a gradient index lens having an error in a refractive index distribution. FIG. 17 is a schematic bar graph showing an example of a Zernike coefficient representing a wavefront aberration of a gradient index lens. In FIG. 17, the horizontal axis represents a term number k, and the vertical axis represents the magnitude of a Zernike coefficient $a_k$. The unit [waves] of the Zernike coefficient $a_k$ represents a designed wavelength λ. FIG. 18 is a schematic graph showing an effect of a method for manufacturing an optical system according to the third embodiment of the present invention. In FIG. 18, the horizontal axis represents a relative rotation angle φ, and the vertical axis represents a Strehl ratio.

As a refractive index distribution n(x, y) in which an astigmatism corresponding to a term number k is distinguished, the following Equation (q) was used.

$$n(x, y) = N_{00}\left\{1 - \frac{\sqrt{A_x}^2}{2}x^2 - \frac{\sqrt{A_y}^2}{2}y^2\right\} \qquad (q)$$

Here, $N_{00}$, √Ax, and √Ay are respectively set to 1.5, 0.595, and 0.605. In addition, by performing ray tracing with D=0.4 (mm) and L=10 (mm), a wavefront aberration of the lens base material 60 was calculated. In this case, P=0.96, and NA=0.1.

FIG. 16 shows a result of ray tracing. In FIG. 16, on-axis luminous fluxes $F_O$ in the yz plane, and off-axis luminous fluxes $F_{0.05}$ of which an image height is 0.05 mm are shown. An image $h_0h$ on a first end face 6a is focused as an image $h_0$"h" on an image surface Ip on an outer side of a second end face 6e as an equal-magnification erecting image.

Zernike coefficients of the wavefront aberration on the image surface Ip are represented as a bar graph shown in FIG. 17. In FIG. 17, a black bar line represents a wavefront aberration of the on-axis luminous fluxes $F_O$, and a white bar line represents a wavefront aberration of the off-axis luminous fluxes $F_{0.05}$.

In all the wavefront aberrations, as represented by the bar lines 202 and 203, an astigmatism of a term number of 4 is distinguished.

Next, a change in the optical performance of a case in which the first lens 6A and the second lens 6B are cut out from such a lens base material 60, and rotation adjustment of the arrangement thereof is performed is represented using a Strehl ratio.

The Strehl ratio is a maximum intensity ratio of a point image intensity distribution. As the Strehl ratio becomes closer to 1, the wavefront aberration becomes better. It is assumed to be practically preferable that the Strehl ratio be equal to or higher than 0.8.

In this simulation, lengths $L_{6A}$ and $L_{6B}$ of the first lens 6A and the second lens 6B were set to L/2=5 [mm].

In the refractive index distribution of an area corresponding to the second lens 6B, ray tracing is performed by rotating the distribution of Equation (q) from 0 degrees to 180 degrees with an increment of 10 degrees. A Strehl ratio was calculated from each wavefront aberration calculated through the ray tracing. A result thereof is shown in FIG. 18.

As shown in FIG. 18, it can be understood that, when the relative rotation angle φ is 90 degrees, the Strehl ratio becomes about 1, and there is almost no aberration. The Strehl ratio has a minimum value when the relative rotation angle φ is 0 degrees and 180 degrees. Under the condition of this simulation, there was almost no difference between the on-axis luminous fluxes $F_O$ and the off-axis luminous fluxes $F_{0.05}$.

From the symmetry of the wavefront aberration of the term number 4, the graph shown in FIG. 18 is assumed to be exactly the same also in a range of the relative rotation angle φ being equal to or larger than 180 degrees and equal to or smaller than 360 degrees.

According to this result, it can be understood that the wavefront aberration of the lens base material 60 and the aberration in a case in which the second lens 6B is rotated by an angle that is an even-number times of 90 degrees reach maximum. On the other hand, it can be understood that, in a case in which the second lens 6B is rotated by an angle that is an odd-number times of 90 degrees, the wavefront aberration reaches a minimum.

According to the result of this simulation, a relative rotation angle φ for which the Strehl ratio was equal to or higher than 0.8 was equal to or higher than 70 degrees and equal to or lower than 110 degrees. Thus, it can be understood that, even when the relative rotation angle φ deviates from odd-number times of 90 degrees by ±20 degrees, practically sufficient optical performance can be acquired.

In other words, in a case in which it is known that an aberration of 2-times rotation symmetry is distinguished through measurement of a wavefront aberration, it is more preferable that the relative rotation angle φ satisfy the following Equation (3) or (4).

$$70 < \varphi < 110 \quad (3)$$

$$250 < \varphi < 290 \quad (4)$$

In a case in which it is known that an aberration of one-time rotation symmetry is distinguished, it is more preferable that the relative rotation angle φ satisfy the following Equation (5).

$$160 < \varphi < 200 \quad (5)$$

In a case in which it is known that an aberration of three-times rotation symmetry is distinguished, it is more preferable that the relative rotation angle φ satisfy any one of the following Equations (6), (7), and (8).

$$40 < \varphi < 80 \quad (6)$$

$$160 < \varphi < 200 \quad (7)$$

$$280 < \varphi < 320 \quad (8)$$

In a case in which it is known that an aberration of four-times rotation symmetry is distinguished, it is more preferable that the relative rotation angle φ satisfy any one of the following Equations (9), (10), and (11).

$$25 < \varphi < 65 \quad (9)$$

$$115 < \varphi < 155 \quad (10)$$

$$295 < \varphi < 335 \quad (11)$$

In addition, in a case in which it is determined to target reduction of a specific aberration in advance, the relative rotation angle φ may be determined in accordance with Equations (3) to (11) without performing measurement in advance.

Next, an aberration reduction effect acquired in an example of a case in which there are a plurality of types of aberration will be described on the basis of a numerical simulation.

Figure 19:
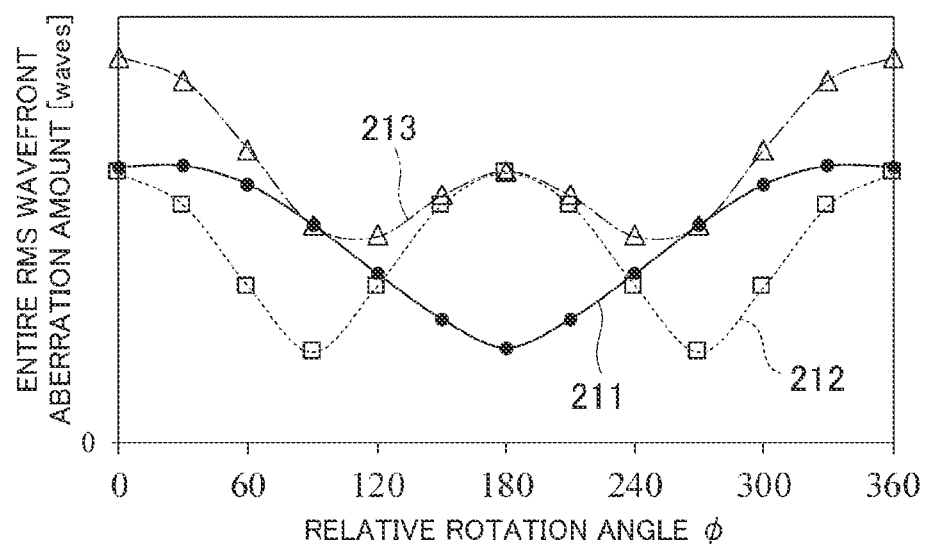
FIG. 19 is a schematic graph showing an aberration reduction effect in an example of a case in which there are a plurality of types of aberration.

FIG. 19 is a schematic graph showing an aberration reduction effect in an example of a case in which there are a plurality of types of aberration. In FIG. 19, the horizontal axis represents a relative rotation angle φ, and the vertical axis represents an RMS wavefront aberration amount [waves] of the entirety. The unit [waves] represents a designed wavelength λ.

As a refractive index distribution n(x, y) capable of causing occurrence of a plurality of types of wavefront aberrations, the following Equation (s) was used.

$$n(x, y) = N_{00}\left\{1 - \frac{\sqrt{A_x}^2}{2}(x+a)^2 - \frac{\sqrt{A_y}^2}{2}y^2\right\} \quad (s)$$

Models 1, 2, and 3 having mutually different refractive index distributions from each other were generated on the basis of Equation (s). Parameters used in each model is represented in the following [Table 2].

TABLE 2

| | On-axis refractive index $N_{00}$ | $\sqrt{A_x}$ | $\sqrt{A_y}$ | a [mm] | L [mm] |
|---|---|---|---|---|---|
| Model 1 | 1.5 | 0.627 | 0.6273 | 0.05 | 25 |
| Model 2 | 1.5 | 0.627 | 0.62745 | 0 | 25 |
| Model 3 | 1.5 | 0.62717 | 0.627 | 0.05 | 25 |

By performing ray tracing for a lens base material 60 of each of Models 1, 2, and 3, wavefront aberration of each lens base material 60 was calculated. In the following [Table 3], a wavefront aberration (RMS) of each term number k of each of Models 1, 2, and 3 is represented. A wavefront aberration of a term number not written in [Table 3] is 0.

TABLE 3

| Term | Wavefront aberration (RMA) [waves] | | | | |
|---|---|---|---|---|---|
| number k | 4 | 7 | 8 | 12 | 13 |
| Model 1 | 0.0003 | 0.0002 | 0.0244 | 0.0002 | 0.0082 |
| Model 2 | 0.0237 | 0 | 0 | 0 | 0.0084 |
| Model 3 | 0.024 | 0.0002 | 0.0242 | 0.0002 | 0.0082 |

As represented in [Table 3], a wavefront aberration that is distinguished in Model 1 was an aberration of k=8 (a coma aberration of the third order, 1-time rotation symmetry). A wavefront aberration that is distinguished in Model 2 was an aberration of k=4 (an astigmatism, 2-times rotation symmetry). Wavefront aberrations that are distinguished in Model 3 were both aberrations of k=4 and 8. The aberration amounts of the distinguished wavefront aberrations were about 0.024 and were approximately equal to each other.

Models 1 to 3 commonly had an approximately equal amount of spherical aberration (k=13).

Next, a simulation of a change in the optical performance in a case in which the first lens 6A and the second lens 6B are cut out from such a lens base material 60, and rotation adjustment of arrangement of each of the lenses was performed. Here, lengths $L_{6A}$ and $L_{6B}$ of the first lens 6A and the second lens 6B were set to L/2=12.5 [mm], and an increment in the rotation angle was set to 30 degrees.

A simulation method of rotation adjustment was similar to that shown in FIG. 18. A result thereof is shown in FIG. 19. In FIG. 19, Curves 211, 212, and 213 respectively represent results of Models 1, 2, and 3.

As shown in Curve 211, in Model 1, the aberration amount was a minimum when the relative rotation angle φ was 180 degrees. The reason for this is assumed to be the coma aberration of k=8 having one-time rotation symmetry. The reason of the aberration amount not being 0 is that Model 1 has a spherical aberration. The spherical aberration is an axis-symmetry aberration, and thus the aberration amount does not change in accordance with rotation of the second lens 6B.

As shown in Curve 212, the aberration amount was a minimum when the relative rotation angle φ was 90 degrees and 270 degrees in Model 2. The reason for this is assumed to be the astigmatism of k=4 having 2-times rotation symmetry. The reason of the aberration amount not being 0 is that there is a spherical aberration of the same level as Model 1.

As shown in Curve 213, Model 3 has aberrations of k=4 and 8 with the same level, and thus aberration amounts at the time of the relative rotation angle being 0 degrees and 360 degrees (a reference rotation position) are larger than those of Models 1 and 2.

The aberration amounts for the relative rotation angle φ of 90 degrees and 270 degrees approximately coincide with the aberration amounts of Model 2. The reason for this is assumed to be that, in a case in which φ is 90 degrees and 270 degrees, the aberration amount of the coma aberration is about 0.

An aberration amount for the relative rotation angle φ of 180 degrees approximately coincides with an aberration amount of Model 1. The reason for this is assumed to be that, in a case in which φ is 180 degrees, the aberration amount of the astigmatism is about 0.

In addition, an aberration amount represented by Curve 213 is approximately the same as a sum of aberration amounts represented by Curves 211 and 212 for each relative rotation angle φ.

For this reason, as in Model 3, in a case in which there are a plurality of aberrations of N-times rotation symmetry in which N is different, it is known that distributions of aberration amounts of a case in which individual aberrations are distinguished may be overlapped to each other.

For this reason, it can be predicted that the aberration amount is a minimum near an angle of an intersection between Curves 211 and 212 in Model 3. In the case of FIG. 19, the intersections between Curves 211 and 212 are formed near 120 degrees and 240 degrees and approximately coincide with relative rotation angles exhibiting a minimum value of Curve 213.

Thus, in a case in which a plurality of types of aberrations are mixed, a relative rotation angle φ minimizing the aberration of the entirety can be predicted by acquiring amounts of change in the aberrations of a case in which only a mixed aberration is distinguished through a numerical simulation or the like and combining those.

In a gradient index lens, a coma aberration and an astigmatism are non-axial symmetry aberrations that may easily occur particularly in a manufacturing process, and there are many cases in which the aberrations occur with the same amount. In such a case, it can be understood that, for example, when the relative rotation angle φ is set to 120 degrees or 240 degrees, the aberration of the entirety can approach a minimum value.

As described above, according to the method for manufacturing an optical system according to this embodiment, a type of distinguished aberration in the lens base material 60 is measured in advance through measurement or the like, and the second lens 6B is disposed on the basis of a relative rotation angle φ that can minimize the aberration in accordance with the type of the aberration. In accordance with this, the aberration of the gradient index lens group 6 is reduced to a minimum value or a value near the minimum value.

According to the manufacturing method of this embodiment, the aberration of the gradient index lens group 6 can be reduced without performing rotation adjustment, and thus the manufacturing cost can be reduced.

At that time, as reviewed with reference to FIG. 18, the setting accuracy of the relative rotation angle φ has a margin of about ±20 degrees. For this reason, for example, when the reference rotation position of the second lens 6B is marked, the rotation position can be easily set through a visual observation as well.

Similar to the first embodiment, according to the method for manufacturing an optical system of this embodiment, deterioration of the image quality can be reduced without reducing the aberration amount of the gradient index lens.

In addition, in each of the embodiments described above, the case in which the optical system including the gradient index lens group 6 is used in the endoscope 100 classified into a rigid scope has been described as an example. However, the gradient index lens group 6 may be used in an appropriate optical device other than an endoscope such as a needle-type microscope, an optical fiber coupling device, a fiber collimator, or the like.

In each of the embodiments described above, the case in which the first lens 6A is bonded and fixed to the inner cylinder 12 has been described as an example. However, the first lens 6A may be fixed to the inner cylinder 12 using a fixing method other than bonding. For example, the first lens 6A may be fixed to the inner cylinder 12 using press fitting, caulking, or the like.

In each of the embodiments described above, the case in which each lens in the gradient index lens group 6 is bonded and fixed to the inner cylinder 12 or the like has been described as an example. However, for example, lenses of the gradient index lens group 6 may be bonded to each other after completion of rotation adjustment. In such a case, the inner cylinder 12 is not necessarily essential.

In each of the embodiments described above, the case in which each lens in the gradient index lens group 6 is bonded and fixed to the inner cylinder 12 or the like, and thus a mutual relative rotation angle is fixed has been described as an example. However, at least one lens may be configured to be able to be relatively rotated with respect to the other lenses for fine adjustment at the time of being used by a user.

For example, at least one lens may be held to be rotatable in the inner cylinder 12 or the like without being bonded.

For example, at least one lens may be disposed adjacently to a member such as the inner cylinder 12 or another lens through an adhesive in uncured condition and the adhesive may be able to be cured after user's fine adjustment.

In each of the embodiments described above, an example in which the first lens 6A and the second lens 6B are formed in a circular column shape having the same outer diameter as that of the lens base material 60 has been described.

However, after the first lens 6A and the second lens 6B are cut out from the lens base material 60, removal processing and additional processing may be performed on outer peripheral parts of the lenses in a range in which there is no influence on internal optical transmission.

Examples of the removal processing include processing of reducing the diameter of a part or the whole of the outer peripheral part, processing of forming a groove part extending in a peripheral direction or in an axial direction in the outer peripheral part, processing of forming a cross-sectional shape of a part or the whole of an optical axis outer peripheral part into a D shape, processing for a rectangular shape, and the like.

Examples of the additional processing include processing of building up in the outer peripheral part, processing of adding a convex shape in the outer peripheral part, process of adding a rough surface in the outer peripheral part, processing of inserting a ring-shaped member into the outer peripheral part, processing of adding a black coating material, and the like.

In each of the embodiments described above, the case in which the gradient index lens group 6 is held in the inner cylinder 12 has been described as an example. However, the gradient index lens group 6 may be directly held in the outer cylinder 11.

In the third embodiment described above, the example in which the relative rotation angle φ of a rotation position at which the second lens 6B is to be disposed is acquired, and the second lens 6B is disposed at the position of the relative rotation angle φ has been described. However, after the second lens 6B is disposed at the acquired relative rotation angle φ, similarly to the first and second embodiments, adjustment of the rotation position from the position of the relative rotation angle φ to a more optimal rotation position may be performed. In such a case, the amount of adjustment is very small, and thus, an adjustment time can be configured to be shorter than that according to the first and second embodiments.

In the second embodiments described above, an example in which an image of the optical chart 191 is visually observed by the measurer M has been described. However, by capturing an image of the optical chart 191 through the gradient index lens group 6 and performing image processing of image data thereof, evaluation amounts such as image contrast and the like may be calculated. In such a case, automatic determination of an image can be performed.

As above, although the preferred embodiments of the present invention have been described, the present invention is not limited to these embodiments. In a range not departing from the concept of the present invention, additions, omissions, substitutions, and other changes of the configurations can be performed.

In addition, the present invention is not limited to the description presented above and is limited only by the attached claims.

According to each of the embodiments described above, an optical system capable of reducing deterioration of image quality by increasing distribution accuracy of a gradient index lens without reducing an aberration amount and correcting an aberration of the gradient index lens using another optical element can be provided.

The invention claimed is:

1. An optical system comprising a plurality of lenses having refractive index distributions in which a refractive index changes in directions orthogonal to optical axes,
   wherein the optical axes of the plurality of lenses are disposed on the same straight line,
   wherein the plurality of lenses are manufactured on the basis of the same design values relating to an on-axis refractive index and a refractive index distribution constant, and
   wherein, when rotation positions around the optical axes of the plurality of lenses at which a total aberration amount of the plurality of lenses reaches a maximum are set as reference rotation positions for the plurality of lenses, any one of the plurality of lenses is arranged at a position acquired by relatively rotating the reference rotation position around the optical axis.

2. The optical system according to claim 1, wherein the plurality of lenses have on-axis refractive indexes that are the same up to two digits after a decimal point, and wherein, when a ratio of a refractive index distribution coefficient of a lens of which the refractive index distribution coefficient is a maximum to a refractive index 20 distribution coefficient of a lens of which the refractive index distribution coefficient is a minimum among the plurality of lenses is denoted by 9, 4 is equal fo or higher than 1 and equal to or lower than 1.1.

3. The optical system according to claim 2,
   wherein a total pitch P of the plurality of lenses satisfies the following Equation (1):

$$P > \frac{0.25\lambda \times NA}{5 \times D \times N_{00} \times \pi} \tag{1}$$

where λ [nm] is an observation wavelength, NA is a numerical aperture, D [mm] is an outer diameter, and $N_{00}$ is an average on-axis refractive index of the plurality of lenses.

4. The optical system according to claim 1, wherein a ratio γ ($=P_S/P$) of a pitch $P_S$ of a lens of which a length is the shortest among the plurality of lenses to a total pitch P of the plurality of lenses satisfies the following Equation (2):

$$\gamma > 0.5 - \frac{0.25\lambda \times NA}{10\pi \times P \times D \times N_{00}} \tag{2}$$

where λ [nm] is a designed wavelength, NA is a numerical aperture, D [mm] is an outer diameter, and $N_{00}$ is an average of the on-axis refractive indexes of the plurality of lenses.

5. The optical system according to claim 1, wherein a pitch of a lens of which a length is the shortest among the plurality of lenses is equal to or larger than 0.5.

6. The optical system according to claim 1, wherein, when magnitude of a mutual relative rotation angle around the optical axis in two lenses among the plurality of lenses is φ [deg], φ satisfies the following Equation (3) or (4):

$$70 < \varphi < 110 \tag{3}$$

$$250 < \varphi < 290 \tag{4}$$

7. The optical system according to claim 1, wherein, when magnitude of a mutual relative rotation angle around the optical axes in two lenses among the plurality of lenses is φ [deg], φ satisfies the following Equation (5):

$$160 < \varphi < 200 \quad (5).$$

8. The optical system according to claim 1, wherein, when magnitude of a S4 mutual relative rotation angle around the optical axes in two lenses among the plurality of lenses is φ [deg], φ satisfies any one of the following Equations (6), (7), and (8):

$$40 < \varphi < 80 \quad (6)$$

$$160 < \varphi < 200 \quad (7)$$

$$280 < \varphi < 320 \quad (8).$$

9. The optical system according to claim 1, wherein, when magnitude of a mutual relative rotation angle around the optical axes in two lenses among the plurality of lenses is φ [deg], φ satisfies any one of the following Equations (9), (10) and (11):

$$25 < \varphi < 65 \quad (9)$$

$$115 < \varphi < 155 \quad (10)$$

$$295 < \varphi < 335 \quad (11).$$

10. The optical system according to claim 1, wherein a total pitch of any two lenses among the plurality of lenses satisfies the following Equation (12):

$$2n + 0.25 < P < 2n + 0.75 \quad (12)$$

where n is an integer equal to or larger than 0.

11. The optical system according to claim 1, wherein a total pitch of any two lenses among the plurality of lenses satisfies the following Equation (12):

$$\frac{L}{D} > 60 \quad (13)$$

12. A method for manufacturing an optical system, the method comprising:
   forming a plurality of lenses by cutting a lens base material having a specific refractive index distribution in which a refractive index changes in a direction orthogonal to an optical axis in a direction intersecting the optical axis; and
   arranging the plurality of lenses such that, when rotation positions around optical axes of the plurality of lenses at which a total aberration amount of the plurality of lenses reaches a maximum are set as reference rotation positions for the plurality of lenses, a state in which any one of the plurality of lenses is relatively rotated around the optical axis with respect to the reference rotation position is formed, and the optical axes of the plurality of lenses are positioned on the same straight line as each other.

13. The method for manufacturing an optical system according to claim 12, further comprising:
   measuring a wavefront aberration of the lens base material and identifying the reference rotation position before the forming of the plurality of lenses; and
   evaluating an aberration amount according to a type of aberration in the wavefront aberration,
   wherein, when the plurality of lenses are arranged, the rotation positions of the plurality of lenses with respect to the reference rotation position are determined such that non-axial symmetry aberrations not having axial symmetry among types of aberrations offset each other.

14. The method for manufacturing an optical system according to claim 13, wherein a Zernike coefficient corresponding to the type of aberration is used when the aberration amount is evaluated.

15. The method for manufacturing an optical system according to claim 12, further comprising measuring the total aberration amount while any one of the plurality of lenses is relatively rotated around the optical axis with respect to the reference rotation position or after relative rotation is performed,
   wherein, when the plurality of lenses are arranged, any one of the plurality of lenses is relatively rotated around the optical axis with respect to the reference rotation position until the total aberration amount satisfies a convergence determination condition determined in advance.

16. The method for manufacturing an optical system according to claim 12, further comprising observing an image of an image evaluation chart for the optical system including the plurality of lenses while any one of the plurality of lenses is relatively rotated around the optical axis with respect to the reference rotation position or before or after the relative rotation is performed,
   wherein, when the plurality of lenses are arranged, any one of the plurality of lenses is relatively rotated around the optical axis with respect to the reference rotation position such that sharpness of the observed image is best.

17. An endoscope comprising the optical system according to claim 1.

* * * * *